United States Patent [19]

Gennari et al.

[11] Patent Number: 5,767,282
[45] Date of Patent: Jun. 16, 1998

[54] METHOD FOR THE PREPARATION OF TAXOL AND ITS DERIVATIVES

[75] Inventors: Cesare Gennari; Nicola Mongelli; Ermes Vanotti; Anna Vulpetti, all of Milan, Italy

[73] Assignee: Pharmacia & Upjohn S.p.A., Milan, Italy

[21] Appl. No.: 776,607
[22] PCT Filed: Jun. 4, 1996
[86] PCT No.: PCT/EP96/02409
§ 371 Date: Feb. 20, 1997
§ 102(e) Date: Feb. 20, 1997
[87] PCT Pub. No.: WO97/00870
PCT Pub. Date: Jan. 9, 1997

[30] Foreign Application Priority Data

Jun. 20, 1995 [GB] United Kingdom ............ 9512471

[51] Int. Cl.$^6$ .................. C07D 263/04; C07D 305/14
[52] U.S. Cl. .................. 548/215; 548/239; 549/510; 549/511
[58] Field of Search .................. 549/510, 511; 548/215, 239

[56] References Cited

U.S. PATENT DOCUMENTS 5,476,954 12/1995 Bourzat et al. .................. 549/510

Primary Examiner—Ba K. Trinh
Attorney, Agent, or Firm—Oblon, Spivak, McClelland, Maier & Neustadt, P.C.

[57] ABSTRACT

A process of making taxane derivatives by reacting Baccatin III derivatives with an oxazolidine which contains a thioester substituent at the 4-position.

14 Claims, No Drawings

METHOD FOR THE PREPARATION OF TAXOL AND ITS DERIVATIVES

This application is a 371 of PCT/EP96/02408, dated Jun. 9, 1996.

The present invention refers to a process for the preparation of Taxol, to the oxazolidine or oxazoline involved in the process and to a process for preparing such oxazolidines or oxazolines.

Taxol, isolated from the bark or several yew species, is considered the most promising cancer chemotherapeutic agent and has recently been approved for treatment of metastatic carcinoma of the ovary. Taxol possesses unusually potent antileukemic and tumor inhibitory properties (Angew. Chem. Int. Ed. Engl. 1994, 33, 15–44). The scarcity and highly challenging structure have stimulated interest in its synthesis. Central to all synthetic strategies for Taxol is the attachment of the C-13 side chain to the baccatin III nucleus, since the presence of this side chain has proven to be essential for the biological activity of Taxol.

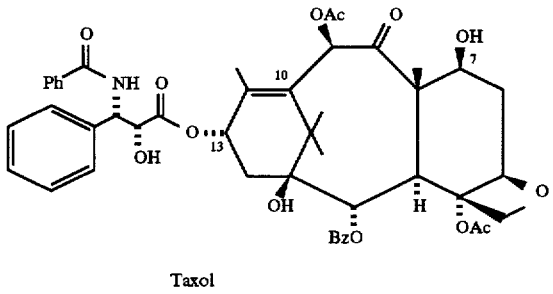

Taxol

The chemical complexity of Taxol dictates that its commercial production by total synthesis is not likely to be economical, while the naturally derived 10-deacetylbaccatin III is readily available in relatively high yield from *T. baccata*. Preparation of quantities of Taxol economically by a semisynthetic approach which involves the condensation of suitably protected N-benzoyl-(2R,3S)-3-phenylisoserine with suitably protected 10-deacetylbaccatin III provides an alternative source of this important natural product and the access to semisynthetic analogues.

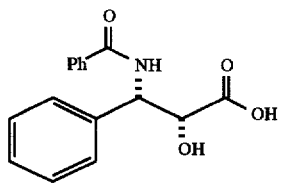

N-benzoyl-(2R, 3S)-3-phenylisoserine

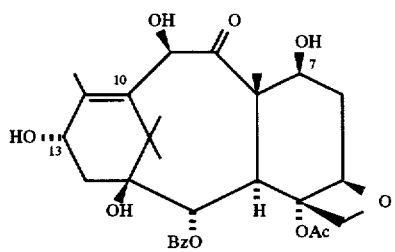

10-deacetylbaccatin III

Therefore, the development of short and practical synthetic routes for phenylisoserine derivatives, as well as of procedures for attachment of the C-13 side chain to the baccatin III nucleus, which are adaptable for industrial-scale production, have become very important.

The numerous papers devoted to the preparation of enantiomerically enriched N-benzoyl-(2R,3S)-3-phenylisoserine include research on semisynthesis drawing from the chiral pool (J.Org.Chem. 1991, 56, 6939; Tetrahedron Lett. 1994, 35, 2845; Synthesis 1995, 181), enzymatic and/or microbial processes (Tetrahedron 1990, 46, 3841; J.Org.Chem. 1993, 58, 1068; J.Org.Chem. 1993, 58, 1287; Tetrahedron Lett. 1994, 35, 9289; Tetrahedron:Asymmetry 1993, 4, 2069; Biotechnol. Appl.Biochem. 1994, 20, 23–33), diastereoselective reactions with covalently-bound chiral auxiliaries or with chiral substrates (J.Org.Chem. 1991, 56, 1681; J.Am.Chem.Soc. 1988, 110, 5917; Tetrahedron Lett. 1991, 32, 3151; J.Chem.Soc., Perkin Trans.1 1993, 1375; Tetrahedron Lett. 1992, 33, 5185; Tetrahedron:Asymmetry 1992, 3, 1007; Tetrahedron 1992, 48, 6985; Synlett 1992, 761; J.Am.Chem.Soc. 1993, 115, 1151; J.Org.Chem. 1994, 59, 1238; J.Org.Chem. 1993, 58, 5889; PCT WO 93 17.997; Tetrahedron 1994, 50, 2785; Tetrahedron 1993, 49, 8323; J.Med.Chem. 1992, 35, 4230; Tetrahedron Lett. 1993, 34, 6049; Bioorg.Med.Chem.Let. 1993, 3, 2467; Bioorg.Med.Chem.Let. 1993, 3, 2475; Bioorg.Med.Chem.Let. 1994, 4, 1381; PCT WO 94 07.847; U.S. Pat. No. 5,294,737; J.Chem.Soc., Perkin Trans.1 1994, 2385), asymmetric catalysis (J.Org.Chem. 1986, 51, 46; J.Org.Chem. 1990, 55, 1957; J.Org.Chem. 1992, 57, 4320; J.Org.Chem. 1994, 59, 5104; Tetrahedron 1992, 48, 10515; J.Chem.Soc., Chem.Commun. 1994, 21; Tetrahedron 1994, 50, 4323; Tetrahedron Lett. 1995, 36, 2063), and chemical resolution of racemic acids (J.Org.Chem. 1993, 58, 255; Tetrahedron: Asymmetry 1994, 5, 1683).

On the other side, only a few reactions have been developed to is attach the "side chain" to the free C-13 OH group of baccatin derivatives. This esterification reaction appears to be hampered by the relevant steric hindrance around the C-13 OH group. Essentially only two general methods have been developed to solve this problem: the first one relies on the DCC Rhone-Poulenc/Gif protocol (J.Am.Chem.Soc. 1988, 110, 5917; Tetrahedron Lett. 1992, 33, 5185, EP 336840, 1989), and the second one on the β-lactam Holton-Ojima protocol (European Patent Application 400971, 1990; U.S. Pat. No. 5,015,744, 1991; Chem. Abstr. 1990, 114, 164568q; U.S. Pat. No. 5,136,060, 1992; U.S. Pat. No. 5,175,315, 1992; P.T.C.Patent Application WO 93/06079, 1993; U.S. Pat. No. 5,229,526, 1993; U.S. Pat. No. 5,283,253, 1994; Med.Chem.Lett. 1992, 2, 295; J.Am.Chem.Soc. 1995, 117, 624; J.Am.Chem.Soc. 1994, 116, 1597; J.Med.Chem. 1994, 37, 1408; J.Org.Chem. 1994, 59, 515; Tetrahedron Lett. 1993, 34, 4149; Tetrahedron Lett. 1994, 35, 1665; Nature 1994, 367, 630; Tetrahedron Lett. 1994, 35, 5543; J.Org.Chem. 1994, 59, 6156; J.Med.Chem. 1994, 37, 3337; J.Am.Chem.Soc. 1995, 117, 2409).

Under forcing conditions (excess DCC, DMAP, 75° C. in toluene) coupling of (2R,3S)-N-benzoyl-O-(1-ethoxyethyl)-3-phenylisoserine with suitably protected baccatin III led to the corresponding ester; unfortunately, acylation under the above mentioned conditions led also to the 2'-epimerized compound. In order to prevent epimerization at carbon 2', other esterification procedures have been developed. In particular the use of cyclic derivatives (oxazolidines) allows milder conditions and no epimerization (Tetrahedron Lett. 1992, 33, 5185).

Rhone-Poulenc Rorer Approach
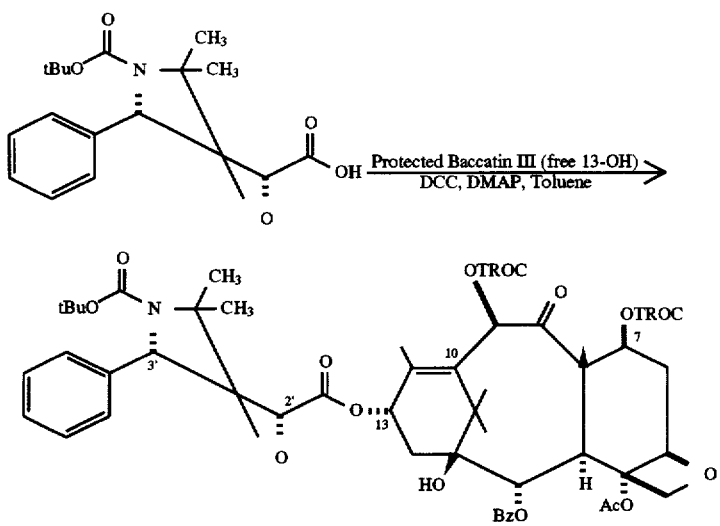
Holton-Ojima Approach
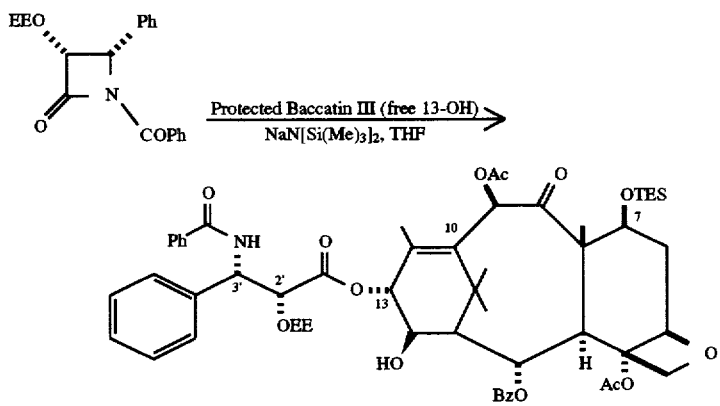
Recently it has been shown that even substrates with the wrong stereochemistry at 2'[(S)] can be transformed into the esterified compounds with the right stereochemistry [2'(R)], using the oxazolidine/DCC approach (Tetrahedron Lett. 1994, 35, 105; PCT/WO 94 10,169).
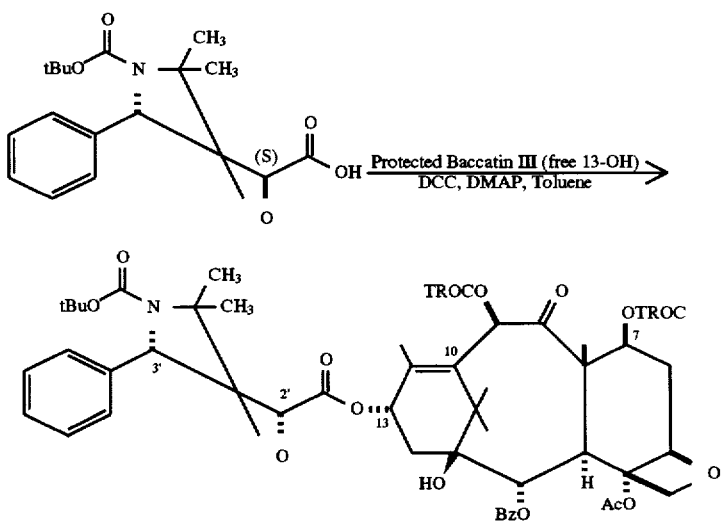

Following a similar route, an oxazoline acid intermediate has been synthesized and used for the DCC coupling reaction with no epimerization (Tetrahedron Lett. 1994, 35, 4483).

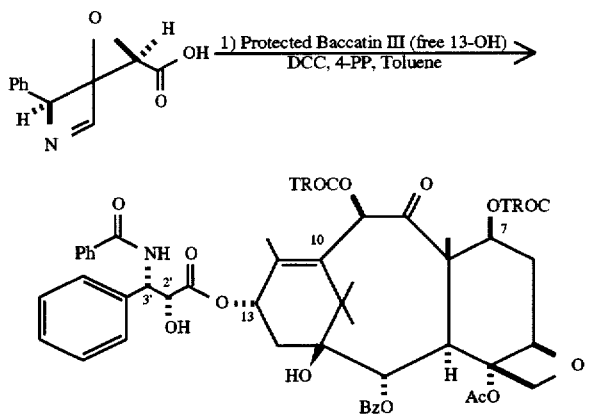

The present invention provides a process for the preparation of a compound of formula (I)

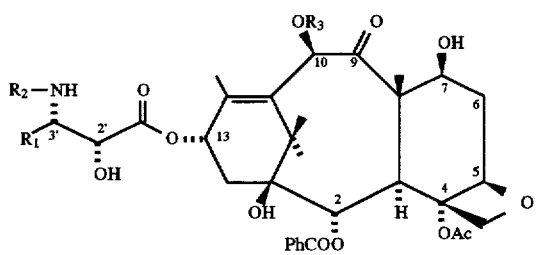

wherein $R_1$ is an aryl or heteroaryl group;

$R_2$ is hydrogen, arylcarbonyl, heteroarylcarbonyl or $C_1$–$C_6$ alkoxycarbonyl;

$R_3$ is hydrogen or acetyl;

the process comprising reacting a compound of formula (II)

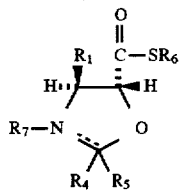

wherein $R_1$ is as defined above, the symbol $\mathrel{=\mkern-3mu=\mkern-3mu=}$ represents a single or a double bond, $R_7$ is $C_1$–$C_6$ alkoxycarbonyl, arylcarbonyl or heteroarylcarbonyl, each of $R_4$ and $R_5$ independently is hydrogen, $C_1$–$C_6$ alkyl, $C_1$–$C_3$ alkoxy, aryl or heteroaryl; and $R_6$ is $C_1$–$C_6$ alkyl, aryl or heteroaryl, provided that when the symbol $\mathrel{=\mkern-3mu=\mkern-3mu=}$ is a double bond, $R_7$ and $R_4$ do not exist and $R_5$ is aryl or heteroaryl, with a compound of formula (III)

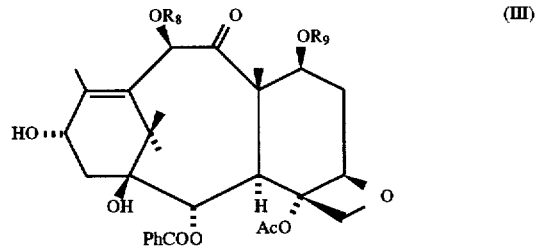

wherein each of $R_8$ and $R_9$ independently is a hydroxy protecting group in the presence of a condensing agent so obtaining a compound of formula (IV)

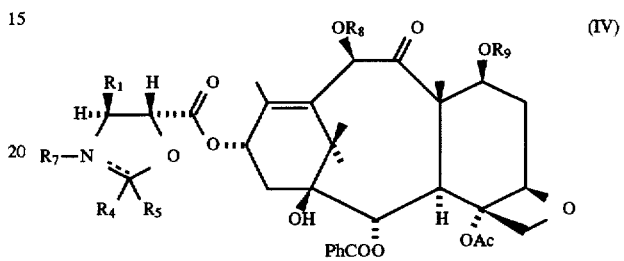

wherein $R_1$, $R_4$, $R_5$, $R_7$, $R_8$ and $R_9$, and the symbol $\mathrel{=\mkern-3mu=\mkern-3mu=}$ are as defined above, provided that when $\mathrel{=\mkern-3mu=\mkern-3mu=}$ is a double bond $R_7$ and $R_4$ do not exist and $R_5$ is aryl or heteroaryl, and deprotecting the compound of formula (IV) under such conditions so as to produce the compound of formula (I), as defined above, and optionally transforming a compound of formula (I) into another compound of formula (I).

Advantages of the invention are the following:
1) High coupling yields between the side chain and the baccatin nucleus via thioester nucleophilic substitution.
2) The synthesis of the taxol side chain is very straightforward (2–4 steps), starting from simple thioester derivatives. The stereochemical control is very high. Both the anti/syn ratio (diastereo-selectivity) and the enantiomeric excesses (enantio-selectivity) are excellent. The desired stereoisomer, out of the possible four, is obtained nearly exclusively during the aldol condensation reaction.
3) The synthesis of the side chain is versatile: different imines and different N-acyl groups can be used without changing the synthetic sequence.

In the formulae of this specification the dotted line ( ····) indicates a substituent in the a configuration, i.e. below the plane of the sheet, and the wedged line ( ◢ ) indicates a substituent in the β configuration, i.e. above the plane of the sheet.

In this specification the alkyl group and the alkoxy group may be straight or branched chain.

An aryl group is for example phenyl, phenyl substituted with $C_1$–$C_6$ alkoxy, halogen, nitro, preferably phenyl.

An heteroaryl group is for example furyl, thienyl or pyridyl, preferably furyl.

A $C_1$–$C_6$ alkoxycarbonyl is, for example, methoxycarbonyl, ethoxycarbonyl, propoxycarbonyl, n-butoxycarbonyl, t-butoxycarbonyl, preferably t-butoxycarbonyl.

Arylcarbonyl is, for example, benzoyl, p-methylbenzoyl, p-chlorobenzoyl, p-trifluoromethylbenzoyl, preferably benzoyl.

Heteroarylcarbonyl is, for example, furylcarbonyl, thienylcarbonyl, pyridylcarbonyl, preferably furylcarbonyl.

A $C_1$–$C_6$ alkyl preferably is methyl, ethyl, propyl, isopropyl, n-butyl, t-butyl, neo-pentyl, preferably methyl, ethyl, t-butyl.

A hydroxy protecting group preferably is 2,2,2-trichloroethoxycarbonyl (TROC), acetyl (Ac), trimethylsilyl, dimethylphenylsilyl, isopropyldimethylsilyl, triethylsilyl (TES), most preferably triethylsilyl, 2,2,2-trichloroethoxycarbonyl, acetyl.

$R_1$ preferably is phenyl, 2-furyl, 4-pyridyl, 4-methoxyphenyl, most preferably phenyl;

$R_2$ preferably is, hydrogen, benzoyl, t-butoxycarbonyl, p-chlorophenylcarbonyl, p-methylphenylcarbonyl, most preferably benzoyl, t-butoxycarbonyl;

$R_3$ preferably is hydrogen, acetyl;

$R_4$ and $R_5$ preferably are hydrogen, $C_1$–$C_6$ alkyl, $C_1$–$C_3$ alkoxy, phenyl or a phenyl group substituted by one or more $C_1$–$C_4$ alkoxy group, most preferably methyl, ethyl, methoxy, phenyl, 2,4-dimethoxyphenyl, 3,4-dimethoxyphenyl or 4-methoxyphenyl.

$R_6$ preferably is a $C_1$–$C_4$ alkyl or phenyl or pyridyl, most preferably t-butyl or phenyl.

$R_7$ preferably is ethoxycarbonyl, n-propoxycarbonyl, n-butoxycarbonyl, t-butoxycarbonyl, benzoyl, p-chlorophenylcarbonyl, p-methylphenylcarbonyl, most preferably benzoyl or t-butoxycarbonyl.

$R_8$ preferably is acetyl or 2,2,2-trichloroethoxycarbonyl.

$R_9$ preferably is phenyldimethylsilyl, triethylsilyl, 2,2,2-trichloroethoxycarbonyl, most preferably triethylsilyl and 2,2,2-trichloroethoxycarbonyl.

The condensing agent may be, for example, a compound of formula (V)

$$MN[Si(R)_3]_2 \qquad (V)$$

wherein R is a $C_1$–$C_4$ alkyl and M is Li, Na or K, or a compound such as NaH, n-BuLi, lithiumdiisopropylamide (LDA), $MNH_2$, where M is as defined above.

Most preferably the condensing agent is $LiN[Si(Me)_3]_2$, $NaN[Si(Me)_3]_2$ or $KN[Si(Me)_3]_2$.

The reaction of a compound of formula (II) with a compound of formula (III) in the presence of a condensing agent of formula (I) may be carried out in an aprotic organic solvent, at a temperature ranging form −78° C. to 0° C., typically for a period of from about 5' to about 1 hr.

Preferably the solvent is an aprotic organic solvent, such as tetrahydrofuran, dimethoxyethane or a mixture thereof.

The reaction is suitably performed by adding to a solution of a compound of formula (II) and a compound of formula (III) in an organic solvent under inert atmosphere, a solution of a condensing agent of formula (V) in an aprotic solvent.

Alternatively, the condensing agent may be a thiophilic metal salt, particularly a Cu, Ag or Hg salt, such as a triflate, trifluoroacetate, acetate, mesilate, and the like. The thiophilic metal salts are usually employed in an organic solvent, such as dichloromethane, benzene, acetonitrile, optionally in the presence of a buffering agent (e.g. $NaHPO_4$). The reaction temperature may range from about 0° C. to the reflux temperature of the solvent, with reaction times of from 1 to 24 hours.

The deprotection of the compound of formula (IV) involves the cleavage of the five membered ring of the compound of formula (IV) and the removal of the protecting groups $R_8$ and $R_9$. The five membered ring is typically opened before or during the removal of the protecting groups $R_8$ and $R_9$. If $R_8$ and $R_9$ are acid labile protecting groups, such as triethylsilyl (TES) groups, no reactants may need to be added to carry out the ring-opening reaction other than those used to remove the groups $R_8$ and $R_9$.

In the case where the symbol $\text{---}$ represents a single bond, the ring opening reaction will be followed by the elimination of the group $C(OH)R_4R_5$ attached to the nitrogen atom. Typically, no extra reactants need to be added to effect this elimination. The deprotection of a compound of formula (IV) may be carried out treating the compound of formula (IV) with organic or mineral acids such as formic acid, p-toluenesulfonic acid, methanesulfonic acid, hydrochloric acid, etc., in a suitable solvent, such as ethanol/water, at temperatures ranging from RT to reflux for periods from 30' to 3 hrs.

When 2,2,2-trichloroethoxycarbonyl (TROC) is present as protecting group, additional treatment with, for example, zinc and acetic acid in methanol, at a temperature ranging from RT to 100° C., for a period from 30' to 3 hrs, is required.

When the symbol $\text{---}$ is a single bond preferably the deprotection may be carried out in the presence of an acid such as hydrochloric acid, formic acid, p-toluenesulfonic acid or methanesulfonic acid.

In the case $R_7$ is $C_1$–$C_6$ alkoxycarbonyl, such as t-butoxycarbonyl (BOC) in the presence of a strong acid, such as hydrochloric or formic acid, a compound of formula (I) wherein $R_2$ is hydrogen is obtained, while when methanesulfonic acid or p-toluenesulfonic acid are used a compound of formula (I) wherein $R_2$ is $C_1$–$C_6$ alkoxycarbonyl, such as t-butoxycarbonyl, is obtained.

When the symbol $\text{---}$ is a double bond preferably the deprotection may be carried out with a strong acid, such as hydrochloric acid, preferably at a temperature of about 100° C. A conversion of a compound of formula (I) into another compound of formula (I) is, for example, the acylation of a compound of formula (I) wherein $R_2$ is hydrogen and $R_1$, $R_3$ are as defined above so obtaining a compound of formula (I) wherein $R_2$ is arylcarbonyl, heteroarylcarbonyl or $C_1$–$C_6$ alkoxycarbonyl. The acylation may be carried out as described in Tetrahedron Letters, 33, 5185–88 (1992) using as acylating agent an aroyl or heteroaroylhalide in a solvent, such as ethylacetate and water in the presence of a base, such as $NaHCO_3$, or a $C_1$–$C_6$ dialkyldicarbonate, such as di t-butyl dicarbonate [$(BOC)_2O$] in a solvent, such as THF in the presence of a base, such as $NaHCO_3$.

Optionally, before the acylation, the hydroxy group in position 7 may be protected with a suitable protecting group, such as 2,2,2-trichloroethoxycarbonyl.

In this case, after the acylation, the protecting group is opportunely removed, for example with Zn/AcOH in warm methanol. The invention refers also to a compound of formula (II)

$$R_1 \overset{\overset{O}{\|}}{C}-SR_6 \quad (II)$$

(with H, H substituents and $R_7-N$, $R_4$, $R_5$, O as shown)

wherein the symbol $\text{---}$ represents a single or a double bond;

$R_1$ is aryl or heteroaryl;

each of $R_4$ and $R_5$ independently is hydrogen, $C_1$–$C_6$ alkyl, $C_1$–$C_3$ alkoxy, aryl or heteroaryl;

$R_6$ is $C_1$–$C_6$ alkyl, aryl or heteroaryl;

$R_7$ is $C_1$–$C_6$ alkoxycarbonyl, arylcarbonyl or heteroarylcarbonyl;

provided that when $\text{---}$ is a double bond $R_7$ and $R_4$ do not exist and $R_5$ is aryl or heteroaryl.

Preferred compounds of formula (II) are those wherein the symbol $\text{---}$ is a single or a double bond;

$R_1$ is phenyl;

each of $R_4$ and $R_5$ independently is hydrogen, $C_1$–$C_6$ alkyl, $C_1$–$C_3$ alkoxy, phenyl or a phenyl group substituted with one or more $C_1$–$C_4$ alkoxy group;

$R_6$ is $C_1$–$C_4$ alkyl, phenyl, 2-pyridyl;

$R_7$ is benzoyl or t-butoxycarbonyl; provided that when --- is a double bond $R_4$ and $R_7$ do not exist and $R_5$ is phenyl or a phenyl group substituted by one or more $C_1$–$C_4$ alkoxy group.

Most preferred compounds of formula (II) are those wherein $R_1$ is phenyl;

each of $R_4$ and $R_5$ independently is hydrogen, methyl, ethyl, methoxy, phenyl, 2,4-dimethoxyphenyl, 3,4-dimethoxyphenyl or 4-methoxyphenyl;

$R_6$ is t-butyl or phenyl;

$R_7$ is benzoyl or t-butoxycarbonyl;

provided that when --- is a double bond $R_4$ and $R_7$ do not exist and $R_5$ is phenyl, 2,4-dimethoxyphenyl, 3,4-dimethoxyphenyl or 4-methoxyphenyl.

A compound of formula (II) may be prepared by a process comprising a) reacting a compound of formula (VI)

$$R_{10}-O-CH_2-\overset{\overset{O}{\|}}{C}-SR_6 \qquad (VI)$$

wherein $R_6$ is as defined above and $R_{10}$ is arylcarbonyl, heteroarylcarbonyl, trialkylsilyl or 1-alkoxyalkyl with a boron complex of formula (VII)

$$L_2BX \qquad (VII)$$

wherein L is a chiral ligand and X is a halogen atom, and subsequently with a compound of formula (VIII)

$$R_1-CH=N-Z \qquad (VIII)$$

wherein $R_1$ is as defined above and Z is trialkylsilyl, $C_1$–$C_6$ alkoxycarbonyl, arylcarbonyl, heteroarylcarbonyl, optionally in the presence of an additional Lewis acid, and alternatively:

i) when $R_{10}$ is arylcarbonyl, or heteroarylcarbonyl, and $R_6$ is $C_1$–$C_6$ alkyl, transposing the arylcarbonyl or heteroarylcarbonyl from oxygen to nitrogen, or ii) reacting with $R_7Y$ wherein $R_7$ is as defined above and Y is a leaving group such as halide, azide or $OR_7$, after or before deprotecting the —$OR_{10}$ group to free hydroxy group; so obtaining a compound of formula (IX)

(IX)

wherein $R_1$, $R_6$ and $R_7$ are as defined above; and b) cyclizing the compound of formula (IX) obtained above either:

b') by reacting the compound of formula (IX), prevailingly in the syn configuration, with a compound of formula (X), (XI) or (XII):

$$\begin{array}{c}R_4\\R_5\end{array}\!\!\!>\!\!=\!O \qquad (X)$$

$$\begin{array}{c}R_4\\ \\R_5\end{array}\!\!\!>\!\!\!C\!\!\!<\!\!\!\begin{array}{c}OR_{11}\\ \\OR_{11}\end{array} \qquad (XI)$$

$$\begin{array}{c}R_5\\R_{11}O\end{array}\!\!\!>\!\!=\!CH_2 \qquad (XII)$$

wherein $R_4$ and $R_5$ are as defined in claim 7 and $R_{11}$ is a $C_1$–$C_3$ alkyl group, so obtaining a compound of formula (II) wherein the symbol --- is a single bond, and $R_1$, $R_4$, $R_5$, $R_6$, $R_7$ are as defined above;

or:

b") by reacting the compound of formula (IX), prevailingly in the anti configuration, with a dehydrating agent, so obtaining a compound of formula (II) wherein --- is a double bond, $R_7$ and $R_4$ do not exist and $R_5$ is aryl, heteroaryl.

In particular the variant ii) of the process step a) may be carried out in different ways according to the meaning of $R_6$ and $R_{10}$:

when $R_{10}$ is trialkylsilyl (different from trimethylsilyl) and $R_6$ is aryl or heteroaryl, reacting with $R_7Y$, wherein $R_7$ is as defined above, but different from $C_1$–$C_6$ alkoxycarbonyl, and Y is halide, azide or OR— and deprotecting the hydroxy group, or when $R_{10}$ is trialkylsilyl (different from trimethylsilyl) and $R_6$ is $C_1$–$C_6$ alkyl, reacting with $R_7Y$, wherein $R_7$ is as defined above, and Y is halide, azide or $OR_7$ and deprotecting the hydroxy group, or when $R_{10}$ is trimethylsilyl or 1-alkoxyalkyl, and $R_6$ is aryl or heteroaryl, removing $R_{10}$ in hydrolytic conditions and reacting with $R_7Y$, wherein $R_7$ and Y are as defined above, but $R_7$ different from $C_1$–$C_6$ alkoxycarbonyl, or when $R_{10}$ is trimethylsilyl or 1-alkoxyalkyl, and $R_6$ is $C_1$–$C_6$ alkyl, removing $R_{10}$ in hydrolytic conditions and reacting with $R_7Y$, wherein $R_7$ and Y are as defined above.

Trialkylsilyl may be, for example, trimethylsilyl, triethylsilyl, t-butyldiphenylsilyl, t-butyldimethylsilyl, triisopropylsilyl, preferably trimethylsilyl, t-butyldimethylsilyl.

1-alkoxyalkyl may be, for example, 1-ethoxyethyl, 1-methyl-1-methoxyethyl, tetrahydropyranyl, 1-(isopropoxy)-ethyl, preferably 1-ethoxyethyl.

L is preferably or respectively obtained from (+) and (−) menthone.

A halogen atom is bromine or chlorine, preferably bromine.

A basic buffer is a buffer at a pH ranging from 8 to 8.5, such as, for example, phosphate buffer, preferably phosphate buffer. The reaction according to process step a) may be carried out reacting the thioester of formula (VI) with the chiral boron reagent (VII) in an organic solvent such as ethyl ether, dichloromethane or a mixture thereof, in the presence of a base, such as triethylamine, diisopropylethylamine and the like, preferably triethylamine, at a temperature ranging from −78° C. to 0° C., typically for a time ranging from 5 to 10 hours, so obtaining a boron enolate intermediate. Then the imine derivative of formula (VIII) is added to the reaction mixture at a temperature ranging from −78° C. to RT, typically for a time ranging from 10 to 24 hours.

When in the compound of formula (VIII) Z is arylcarbonyl or heteroarylcarbonyl, the presence of extra-added Lewis acids, e.g., $BF_3 \cdot Et_2O$, $TiCl_4$, $Et_2AlCl$, etc., preferably $BF_3 \cdot Et_2O$, $TiCl_4$, $Et_2AlCl$ may be required for optimal yields.

When in the starting compound (VI) $R_{10}$ is arylcarbonyl, or heteroarylcarbonyl, and $R_6$ is $C_1$–$C_6$ alkyl, the reaction is quenched with phosphate buffer (pH 6) and extracted with a suitable solvent (e.g., dichloromethane). The organic phase is treated with aqueous hydrogen chloride in organic solvent, such as methanol, and concentrated to dryness. The resulting product is washed thoroughly with a solvent, like ethyl ether, and then allowed to react at pH ranging from 8 to 8.5 in buffered methanol-water at a temperature ranging from 0° C. to 25° C., typically for a period of time ranging from 10 to 20 hours, in order to obtain the migration of the arylcarbonyl or heteroarylcarbonyl group from oxygen to nitrogen.

When $R_{10}$ in the starting compound (VI) is trialkylsilyl (different from trimethylsilyl), and $R_6$ is aryl or heteroaryl, then the reaction product is reacted with $R_7Y$, wherein $R_7$ is as defined above but different from $C_1$–$C_6$ alkoxycarbonyl, in an organic solvent, such as pyridine, in the presence of a catalyst, such as 4-dimethylaminopyridine (DMAP), at a temperature ranging from 0° C. to RT, for a time ranging from 20 to 100 hours. The subsequent deprotection of the hydroxy group may be carried out, for example, in the presence of an inorganic acid, such as HF, in an aqueous organic solvent, such as acetonitrile, at a temperature ranging from −20° C. to RT.

When $R_{10}$ in the starting compound (VI) is trialkylsilyl (different from trimethylsilyl), and $R_6$ is $C_1$–$C_6$ alkyl, then the reaction product is reacted with $R_7Y$, wherein $R_7$ is as defined above, in an organic solvent, such as dichloromethane, in the presence of a catalyst, such as 4-dimethylaminopyridine (DMAP), at a temperature ranging from 0° C. to RT, for a time ranging from 20 to 100 hours. The subsequent deprotection of the hydroxy group may be carried out, for example, in the presence of an inorganic acid, such as HF, in an aqueous solvent, such as acetonitrile, or in the presence of pyridinium-HF in an organic solvent, such as THF, at a temperature ranging from −20° C. to RT.

When $R_{10}$ in the starting compound (VI) is an acid labile group (such as alkoxyalkyl, trimethylsilyl, etc.), treatment with aqueous hydrogen chloride in a solvent like MeOH, removes the above mentioned $R_{10}$. Subsequent treatment with $R_7Y$, wherein $R_7$ is as defined above, but is different from $C_1$–$C_6$ alkoxycarbonyl when $R_6$ is aryl or heteroaryl in Schotten-Bauman reaction conditions, for example with a base like $NaHCO_3$ in a mixture of water and organic solvent like dichloromethane, at a temperature ranging from 0° C. to 50° C., for a period of time ranging from 30′ to 5 hours, yields the N-acylated product.

For example, the reaction step a) with the step variant i) is reported herebelow in Scheme 1, for the reaction of a compound of formula (VI) wherein $R_{10}$ is PhCO and $R_6$ is t-butyl with a boron complex of formula (VII) wherein L is derived from (+)menthone and X is bromine and a compound of formula (VIII) wherein $R_1$ is phenyl (Ph) and Z is trimethylsilyl (—SiMe$_3$).

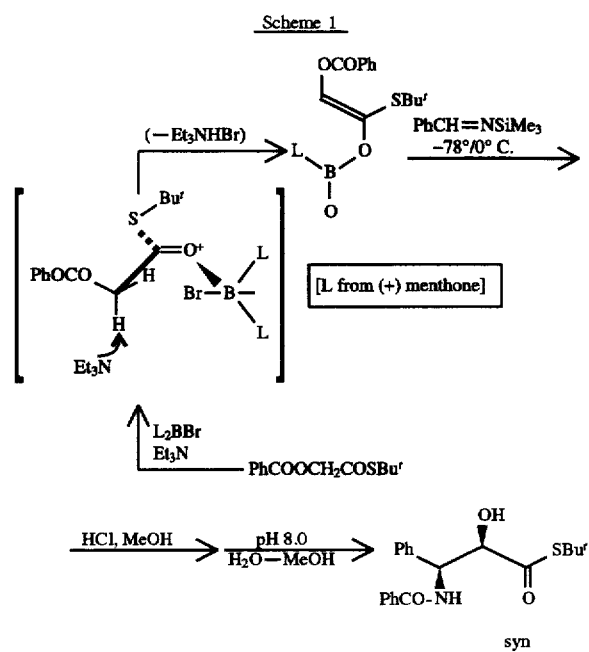

Scheme 1

The glycolate thioester $PhCOOCH_2COSBu^t$ enolizes in $CH_2Cl_2$—$Et_2O$ with the chiral boron reagent $L_2BBr$, in the presence of triethylamine, and the imine derived from benzaldehyde (PhCH=NSiMe$_3$) is added, at −78° C. The reaction is allowed to warm to 0° C., then is quenched with HCl—MeOH—$H_2O$, and evaporated to dryness. The resulting solid is washed several times with ethyl ether, and then allowed to react (—COPh migrates from oxygen to nitrogen) at pH 8.0 in buffered MeOH—$H_2O$. The desired compound (formula IX: $R_1$=Ph; $R_7$=PhCO; $R_6$=Bu$^t$) is obtained practically pure, by simple solvent extraction, without the need of chromatography. The stereochemical control is high (syn:anti≧96:4; %EE≧96). For example, the reaction step a) with the step variant ii) is reported herebelow in Scheme 2, for the reaction of a compound of formula (VI) wherein $R_{10}$ is t-butyl dimethylsilyl (TBDMS) and $R_6$ is phenyl (Ph) with a boron complex of formula (VII) wherein L is derived from (−)menthone and X is bromine, and a compound of formula (VIII) wherein $R_1$ is phenyl (Ph) and Z is trimethylsilyl (—SiMe$_3$).

Scheme 2

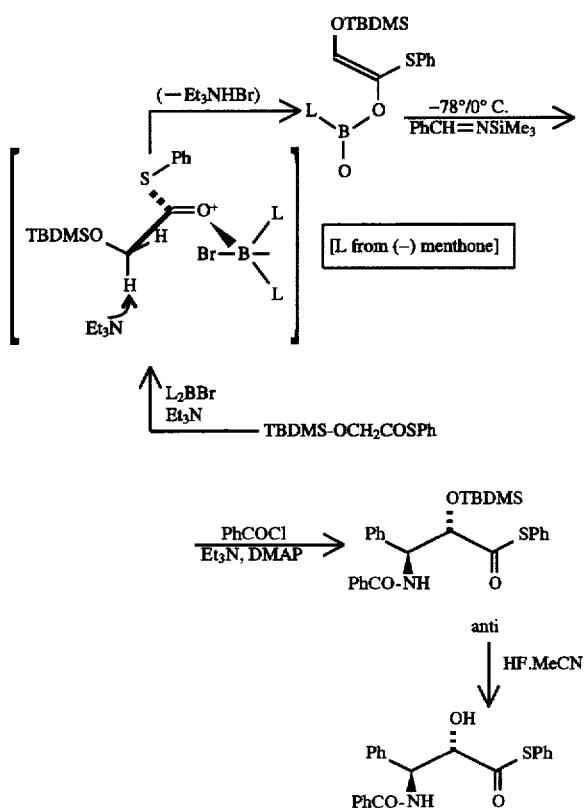

Scheme 3

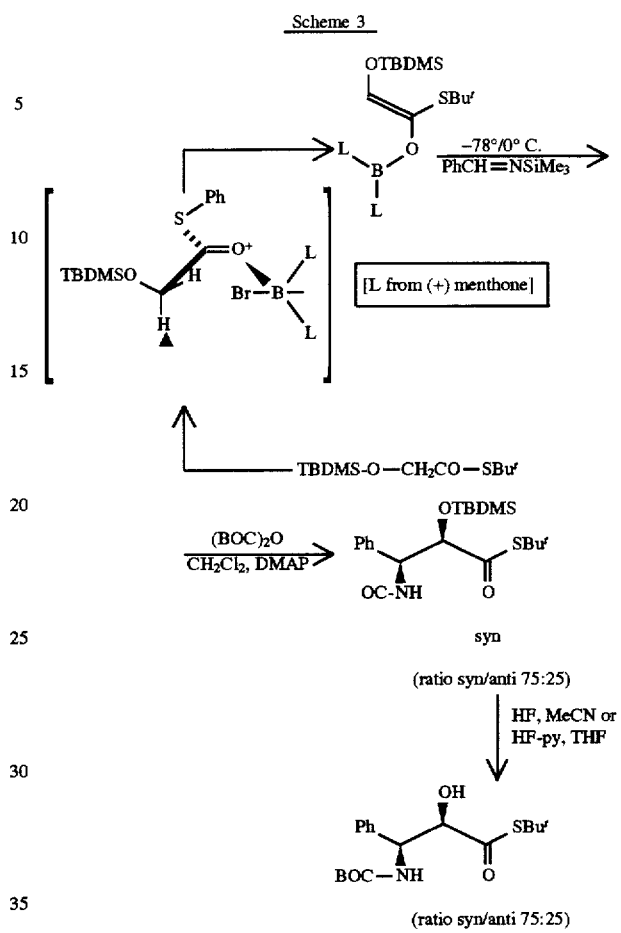

The glycolate thioester TBDMSOCH$_2$COSPh enolizes in CH$_2$Cl$_2$—Et$_2$O with the chiral boron reagent L$_2$BBr, in the presence of triethylamine, and the imine derived from benzaldehyde (PhCH=NSiMe$_3$) is added, at −78° C. The reaction is allowed to warm to 0° C., then is quenched with pH 7 phosphate buffer, and extracted with solvent. The organic residue is treated with 0.25N HCl in MeOH—H$_2$O (1:1 v:v) and evaporated to dryness. The resulting solid is treated in dichloromethane with PhCOCl, Et$_3$N and a catalytic quantity of 4-dimethylaminopyridine (DMAP) to give a product that is purified via flash chromatography. The stereochemical control is high (anti:syn≧97:3; %EE≧95). The obtained product is treated with aqueous HF in acetonitrile to give the desired product (formula IX: R$_1$=Ph; R$_7$=PhCO; R$_6$=Ph).

An example relative to the reaction step a) with the step variant ii) is reported herebelow in Scheme 3, for the reaction of a compound of formula (VI) wherein R$_{10}$ is t-butyldimethylsilyl (TBDMS) and R$_6$ is t-butyl with a boron complex of formula (VII) wherein L is derived from (+)menthone and X is bromine, and a compound of formula (VIII) wherein R$_1$ is phenyl (Ph) and Z is trimethylsilyl (—SiMe$_3$).

The glycolate thioester TBDMSOCH$_2$COSBu$^t$ enolizes in CH$_2$Cl$_2$—Et$_2$O with the chiral boron reagent L$_2$BBr, in the presence of triethylamine, and the imine derived from benzaldehyde (PhCH=NSiMe$_3$) is added, at −78° C. The reaction is allowed to warm to 0° C., then is quenched with pH 7 phosphate buffer and extracted with solvent. The organic residue is treated with excess ditertbutyldicarbonate [(BOC)$_2$O] and DMAP in dichloromethane to give a product (syn:anti≧75:25; %EE≧96) that is treated with aqueous HF in acetonitrile or with HF-pyridine in THF to give the desired product (formula IX):

R$_1$=Ph; R$_7$=BOC; R$_6$=$^t$Bu).

For example, the reaction step a) with the step variant ii) is reported herebelow in Scheme 4, for the reaction of a compound of formula (VI) wherein R$_{10}$ is 1-ethoxyethyl (EE) or trimethylsilyl (TMS) and R$_6$ is phenyl (Ph) with a boron complex of formula (VII) wherein L is derived from (−)menthone and X is bromine, and a compound of formula (VIII) wherein R$_1$ is phenyl (Ph) and Z is trimethylsilyl (—SiMe$_3$).

Scheme 4

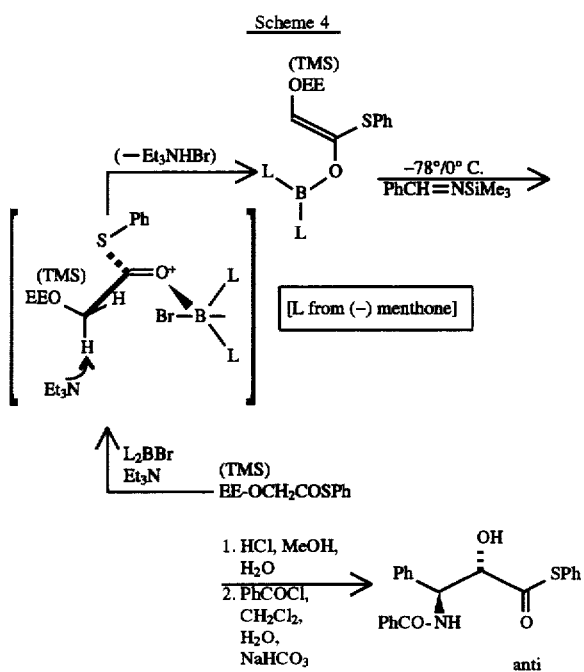

[L from (−) menthone]

The glycolate thioester EEOCH$_2$COSPh or TMSOCH$_2$COSPh enolizes in CH$_2$Cl$_2$—Et$_2$O with the chiral boron reagent L$_2$BBr, in the presence of triethylamine, and the imine derived from benzaldehyde (PhCH=NSiMe$_3$) is added, at −78° C. The reaction is allowed to warm to 0° C., then is quenched with pH 7 phosphate buffer and extracted with solvent. The organic residue is treated with hydrochloric acid and then reacted with benzoyl chloride in a mixture of water and dichloromethane, in the presence of NaHCO$_3$ to give the desired product (formula (IX): R$_1$=Ph; R$_7$=PhCO; R$_6$=Ph) (anti:syn≧99:1; %EE≧85–88).

The reaction between a compound of formula (IX) and a compound of formula (X) or (XI) or (XII), according to the process step b'), is carried out using a compound of formula (IX) having a predominance of the syn configuration as reported herebelow:

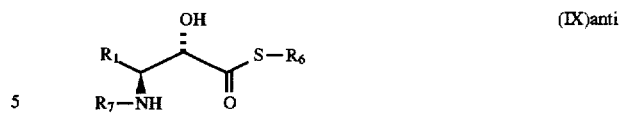

(IX)syn

The reaction may be carried out by adding the compound of formula (X), (XI) or (XII) to a solution of a compound of formula (IX) and a catalyst, such as pyridinium tosylate or p-toluenesulfonic acid in an organic solvent, such as toluene, at a temperature ranging from 0° C. to 100° C., typically for a time ranging from 30' to 2 hours. During this process, the minor anti-stereoisomer of the compound of formula (IX) doesn't cyclize and can be therefore easily removed by simple chromatographic techniques.

For example, 2-methoxypropene (formula XII: R$_5$=CH$_3$; R$_{11}$=CH$_3$) or 2,2-dimethoxypropane (formula XI: R$_4$, R$_5$, R$_{11}$=CH$_3$) is added to a solution of a compound of formula (IX) and pyridinium tosylate or p-toluenesulfonic acid in toluene at a temperature ranging from room temperature to 80° C., for a time of about 1 hour.

The cyclization of a compound of formula (IX) according to the process step b"), is carried out using a compound of formula (IX) having a predominance of the anti-configuration as reported herebelow:

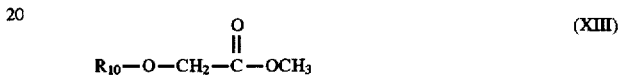

(IX)anti

The reaction may be carried out adding to a solution of a compound of formula (IX) in an organic solvent, such as 1,2-dichloroethane, a dehydrating agent such as thionylchloride at a temperature between room temperature and the reflux temperature of the solvent for a time ranging from 1 to 5 hours.

During this process, the minor syn stereoisomer of a compound of formula (IX) does not cyclize and can be therefore easily removed by simple chromatographic techniques. A compound of formula (VI) may be obtained accordingly with the nature of R$_6$ and R$_{10}$, in general by transesterification of a compound of formula (XIII)

$$R_{10}-O-CH_2-\overset{O}{\underset{\|}{C}}-OCH_3 \qquad (XIII)$$

wherein R$_{10}$ is hydrogen, trialkylsilyl, 1-alkoxyalkyl with a thiol of formula (XIV)

$$R_6-SH \qquad (XIV)$$

wherein R$_6$ is as defined above.

When R$_{10}$ is hydrogen atom in the compound of formula (XIII), or has become hydrogen atom in the compound of formula (VI), during the transesterification reaction, the hydroxy group is reacted with convenient protecting groups, for example with arylcarbonyl halides, heteroarylcarbonyl halides, trialkylsilyl halides or alkylvinyl ethers.

The transesterification reactions may be carried out in a solvent, such as methylene chloride, in the presence of trialkylaluminium, such as trimethylaluminium at a temperature from about 0° C. to about room temperature for a time ranging from 10 minutes to 24 hours.

A compound of formula (XIII) is commercially available methylglycolate or may be obtained by reaction of methylglycolate with compounds, such as trialkylsilyl halides, aroyl halides, heteroaroyl halides, in the presence of a base (e.g. triethylamine), or alkylvinyl ethers, in the presence of a catalyst like p-toluenesulfonic acid in a solvent like THF.

The compounds of formula (III) may be achieved from commercially available 10-deacetyl baccatin III by means of methods reported in literature (C. R. Sciences, Acad.Sci. Paris, serie 2, 1984, 24, 1039; Tetrahedron 1986, 42, 4451; J.Med.Chem. 1991, 34, 992; JACS 1988, 110, 5917).

The boron complex of general formula (VII) can be prepared as described in literature (J.O.C. 1992, 57, 5173; Angew-Chem.Int. Ed. Engl. 1993, 32, 1618).

The imines of general formula (VIII) can be prepared as described in literature (J.O.C. 1983, 48, 289; Synthesis 1984, 628; J.O.C. 1993, 53, 5889; J.O.C. 1994, 59, 1238).

The compounds of formula (X), (XI), (XII), (XIII) and (XIV) are commercially available.

EXAMPLE 1

7,10-di(2,2,2-trichloroethyloxycarbonyl)-10-deacetyl-13-O-[(4S, 5R)-2,4-diphenyl-4,5-dihydrooxazole-5-carbonyl]-baccatin (Compound of formula IV:---=double bond; R$_1$=Ph; R$_5$=Ph;

17

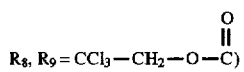

A solution of 7,10-di(2,2,2-trichloroethyloxycarbonyl)-10-deacetylbaccatin III (Compound III:

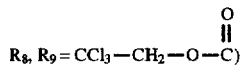

(28.3 mg, 0.032 mmol) and phenyl (4S,5R)-2,4-diphenyl-4,5-dihydrooxazole-5-thiocarboxylate (Compound II: --- =double bond; $R_1$=Ph; $R_5$=Ph; $R_6$=Ph) (38.4 mg, 0.107 mmol) in THF (0.6 ml) at 0° C. under argon, with stirring, was treated with a freshly prepared 0.6M solution of lithium hexamethyldisilazide in THF-hexanes 62:38 (0.237 ml, 0.142 mmol). After 15 min stirring at 0° C., the mixture was quenched with a saturated $NH_4Cl$ aqueous solution (2 ml). The aqueous phase was extracted with ethyl ether (3×3 ml), and the combined organic extracts were dried ($Na_2SO_4$) and evaporated. The crude product was purified by flash chromatography (hexanes-ethyl acetate 7:3) to give the pure title compound (32.5 mg, 90%).

$[\alpha]_D^{25}$=−40.5° (c 1.0 in chloroform).

$^1$H-NMR ($CDCl_3$) $\delta$=1.21 (3H, s, Me), 1.29 (3H, s, Me), 1.87 (3H, s, Me), 2.03 (3H, s, Me), 2.07 (3H, s, OCOMe), 1.95–2.2 (1H, m, C6-H), 2.35 (1H, A of an ABX system, JAB=15.04, JAX=8.68 Hz, C14-H), 2.36 (1H, B of an ABX system, JAB=15.04, JBX=9.14 Hz, C14-H), 2.68 (1H, ddd, J=7.24, 9.48, 14.5 Hz, C6-H), 3.95 (1H, d, J=7.00 Hz, C3-H), 4.17 (1H, d, J=8.61 Hz, C20-H), 4.33 (1H, d, J=8.61 Hz, C20-H), 4.62 (1H, d, J=11.85 Hz, C—H [troc]), 4.74 (1H, d, J=12.0 Hz, C—H [troc']), 4.82 (1H, d, J=12.0 Hz, C—H [troc']), 4.92 (1H, d, J=11.85 Hz, C—H [troc]), 4.98 (1H, d, J=6.95 Hz, C3'-H), 4.99 (1H, d, J=9.48 Hz, C5-H), 5.59 (1H, m, C7-H), 5.60 (1H, d, J=6.95 Hz, C2'-H), 5.71 (1H, d, J=7.00 Hz, C2-H), 6.25 (1H, s, C10-H), 6.28 (1H, m, C13-H), 7.30–7.70 (11H, m, Ar—H), 8.08 (2H, d, J=7.3 Hz, Ar—H), 8.21 (2H, d, J=6.81 Hz, Ar—H).

$^{13}$C NMR ($CDCl_3$) selected peaks $\delta$=10.63, 14.67, 20.83, 21.50, 26.25, 33.11, 35.44, 42.98, 46.82, 56.07, 71.58, 74.10, 74.73, 76.13, 77.29, 78.87, 80.37, 83.35, 83.56, 94.07, 126.20, 126.71, 128.28, 128.64, 129.00, 130.00, 132.12, 132.22, 133.88, 140.61, 142.23, 153.04, 166.80, 169.92, 200.60.

MS(FAB+): 1142 (M+H+, 56%), 1143 (M+2, 36%), 1144 (M+3, 100%), 1145 (M+4, 59%), 1146 (M+5, 92%), 1147 (M+6, 46%), 1148 (M+7, 46%), 1149 (M+8, 21%), 1150 (M+9, 13%), 1164 (M+Na+, 36%), 1165 (M+24, 23%), 1166 (M+25, 69%), 1167 (M +26, 41%), 1168 (M+27, 61%), 1169 (M+28, 33%), 1170 (M+29, 31%), 1171 (M+30, 15%), 1172 (M+31, 10%).

EXAMPLE 2

7,10-di(2,2,2-trichloroethyloxycarbonyl)-10-deacetyl-13-O-[(4S, 5R)-2,4-diphenyl-4,5-dihydrooxazole-5-carbonyl]-baccatin (Compound of formula IV: ---=double bond; $R_1$=Ph; $R_5$=Ph; $R_8,R_9$=$CCl_3$—$CH_2$—O—CO—)

To a magnetically stirred solution of 7,10-di(2,2,2-trichloroethyloxycarbonyl)-10-deacetyl baccatin III (10.4 mg, 0.012 mmol) and phenyl (4S,5R)-2,4-diphenyl-4,5-dihydrooxazole-5-thiocarboxylate (12.53 mg, 0.035 mmol) in $CH_2Cl_2$ (0.120 ml) at RT, under argon, $Ag(CF_3COO)$ (10.16 mg, 0.046 mmol) was added. After overnight stirring at room temperature, the mixture was diluted with methyl-

18 ene chloride, filtered through celite, and washed with a saturated $NH_4Cl$ aqueous solution (1 ml). The organic phase was dried ($Na_2SO_4$) and evaporated. The crude product was purified by flash chromatography (hexanesethyl acetate 7:3) to give the pure title compound (5.1 mg, 36%).

EXAMPLE 3

7,10-di(2,2,2-trichloroethyloxycarbonyl)-10-deacetyl-13-O-[(4S, 5R)-2,4-diphenyl-4,5-dihydrooxazole-5-carbonyl]-baccatin (Compound of formula IV: --- =double bond; $R_1$=Ph; $R_5$=Ph;

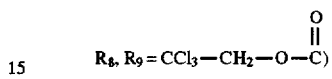

To a magnetically stirred solution of 7,10-di(2,2,2-trichloroethyloxycarbonyl)-10-deacetyl baccatin III (15.0 mg, 0.017 mmol) and phenyl (4S,5R)-2,4-diphenyl-4,5-dihydrooxazole-5-thiocarboxylate (24.0 mg, 0.067 mmol) in benzene (0.170 ml) at RT, under argon, $Ag(CF_3COO)$ (15 mg, 0.067 mmol) and $Na_2HPO_4$ (18.9 mg, 0.05 mmol) were added. After 36 hours stirring at room temperature, the mixture was diluted with methylene chloride, filtered through celite, and washed with a saturated $NH_4Cl$ aqueous solution (1 ml). The organic phase was dried ($Na_2SO_4$) and evaporated. The crude product was purified by flash chromatography (hexanes-ethyl acetate 7:3) to give the pure title compound (10.5 mg, 51%).

EXAMPLE 4

7-triethylsilyl-13-O-[(4S,5R)-2,4-diphenyl-4,5-dihydrooxazole-5-carbonyl]-baccatin (Compound of formula IV: --- =double bond; $R_1$=Ph; $R_5$=Ph;

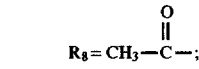

A solution of 7-TES-baccatin III (Compound III:

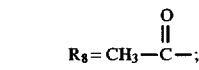

$R_9$=$(CH_3$—$CH_2$—$)_3Si$—) (199 mg, 0.284 mmol) and phenyl (4S,5R)-2,4-diphenyl-4,5-dihydrooxazole-5-thiocarboxylate (Compound II: ---=double bond; $R_1$=Ph; $R_5$=Ph; $R_6$=Ph) (357 mg, 0.994 mmol) in THF (5.68 ml) at 0° C. under argon, with stirring was treated with a freshly prepared 0.6 M solution of lithium hexamethyldisilazide in THF-hexanes 62:38 (2.13 ml, 1.28 mmol). After 15 min stirring at 0° C., the mixture was quenched with a saturated $NH_4Cl$ aqueous solution (14 ml). The aqueous phase was extracted with ethyl ether (3×20 ml), and the combined organic extracts were dried ($Na_2SO_4$) and evaporated. The crude product was purified by flash chromatography (pentanes-ethyl ether 44:56) to give pure title compound (230 mg, 85%).

$[\alpha]_D^{25}$=−54.8° (c 1.0 in chloroform).

$^1$H-NMR ($CDCl_3$) $\delta$=0.60 (6H, q, J=7.29 Hz, $CH_2Si$), 0.94 (9H, t, J=7.29 Hz, Me[TES]), 1.21 (3H, s, Me), 1.25 (3H, s, Me), 1.71 (3H, s, Me), 2.01 (3H, s, Me), 2.08 (3H, s, OCOMe), 2.18 (3H, s, OCOMe), 1.95–2.2 (1H, m, C6-H), 2.22–2.45 (2H, m, C14-H), 2.55 (1H, m, C6-H), 3.85 (1H, d, J=6.99 Hz, C3-H), 4.15 (1H, d, J=8.34 Hz, C20-H), 4.31

19

(1H, d, J=8.34 Hz, C20-H), 4.51 (1H, dd, J=6.59, 10.29 Hz, C7-H), 4.96 (1H, d, J=6.51 Hz, C3'-H), 4.96 (1H, d, C5-H), 5.62 (1H, d, J=6.51 Hz, C2'-H), 5.70 (1H, d, J=6.99 Hz, C2-H), 6.21 (1H, br. t, J=8.80 Hz, C13-H), 6.44 (1H, s, C10-H), 7.30–7.70 (11H, m, Ar—H), 8.09 (2H, d, J=7.24 Hz, Ar—H), 8.25 (2H, d, J=7.79 Hz, Ar—H).

$^{13}$C NMR (CDCl$_3$) selected peaks δ=5.17, 6.66, 9.93, 14.43, 20.74, 21.60, 26.45, 29.58, 35.48, 37.05, 43.07, 46.90, 58.34, 71.79, 72.19, 74.67, 74.87, 78.90, 80.77, 83.24, 84.10, 126.31, 126.60, 128.17, 128.51, 128.88, 129.97, 132.05, 133.64, 133.93, 139.75, 140.68, 166.91, 169.05, 169.77, 170.09, 201.60.

MS(FAB+): 950 (M+H+, 71%), 951 (M+2, 43%), 952 (M+3, 21%), 972 (M+Na+, 100%), 973 (M+24, 64%), 974 (M+25, 28%).

EXAMPLE 5

7,10-di(2,2,2-trichloroethyloxycarbonyl)-10-deacetyl-13-O-[(4S, 5R)-N-benzoyl-2,2-dimethyl-4-phenyl-1,3-oxazolidin-5-carbonyl]-baccatin (Compound of formula IV:=single bond; R$_1$=Ph; R$_4$,R$_5$=CH$_3$;

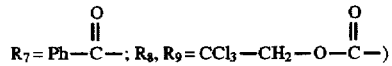

A solution of 7,10-di(2,2,2-trichloroethoxycarbonyl)-10-deacetylbaccatin III (Compound III:

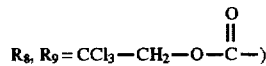

(24.4 mg, 0.027 mmol) and t-butyl [(4S,5R)-N-benzoyl-2,2-dimethyl-4-phenyl-1,3-oxazolidin-5-yl]thiocarboxylate (Compound II: =single bond; R$_1$=Ph; R$_4$,R$_5$=CH$_3$; R$_6$=t-butyl; R$_7$=Ph—CO) (40.2 mg, 0.101 mmol) in THF (0.545 ml) at 0° C. under argon, with stirring, was treated with a freshly prepared 0.6M solution of lithium hexamethyldisilazide in THF-hexanes 62:38 (0.090 ml, 0.054 mmol). After 24 h stirring at 0° C., the mixture was quenched with a saturated NH$_4$Cl aqueous solution (2 ml). The aqueous phase was extracted with ethyl ether (3×3 ml), and the combined organic extracts were dried (Na$_2$SO$_4$) and evaporated. The crude product was purified by flash chromatography (hexanes-ethyl acetate 6:4) to give the pure title compound (24.6 mg, 75%).

[α]$_D^{25}$=−28.90 (c 1.0 in chloroform)

$^1$H-NMR (CDCl$_3$) δ=1.20 (3H, s, Me), 1.28 (3H, s, Me), 1.74 (3H, s, Me), 1.93 (3H, S, Me), 1.98 (3H, s, Me), 2.02 (3H, s, Me), 2.20 (3H, s, OCOMe), 1.95–2.2 (1H, m, C6-H), 2.20–2.40 (2H, m, C14-H), 2.50–2.70 (1H, m, C6-H), 3.91 (1H, d, J=6.95 Hz, C3-H), 4.11 (1H, d, J=8.60 Hz, C20-H), 4.29 (1H, d, J=8.60 Hz, C20-H), 4.58 (1H, d, J=4.10 Hz, C2'-H), 4.62 (1H, d, J=10.58 Hz, C—H [troc]), 4.65–4.91 (2H, m, C—H [troc]), 4.94 (1H, d, J=10.58 Hz, C—H [troc]), 4.92 (1H, m, C5-H), 5.30 (1H, d, J=4.10 Hz, C3'-H), 5.60 (1H, dd, J=6.80, 9.92 Hz, C7-H), 5.67 (1H, d, J=6.95 Hz, C2-H), 6.27 (1H, s, C10-H), 6.30 (1H, m, C13-H), 6.90–7.00 (2H, m, Ar—H), 7.10–7.30 (8H, m, Ar—H), 7.40–7.70 (3H, m, Ar—H), 8.09 (2H, d, J=8.00 Hz, Ar—H).

$^{13}$C NMR (CDCl$_3$) selected peaks δ=10.63, 14.62, 20.94, 21.50, 26.15, 29.58, 29.93, 33.07, 35.20, 42.97, 46.82, 55.96, 65.75, 71.31, 74.11, 76.03, 77.29, 78.89, 80.32, 81.18, 83.57, 94.07, 98.21, 126.06, 126.82, 127.82, 127.98, 128.54, 128.63, 128.85, 129.39, 129.95, 133.78, 137.38, 138.69, 142.43, 153.09, 166.79, 168.98, 169.96, 200.54.

20

MS(FAB+): 1198 (M−1, 29%), 1199 (M, 20%), 1200 (M+H+, 50%), 1201 (M+2, 33%), 1202 (M+3, 45%), 1203 (M+4, 29%), 1204 (M+5, 23%), 1205 (M+6, 13%), 1206 (M+7, 12%), 1220 (M+21, 45%), 1221 (M+22, 30%), 1222 (M+Na+, 100%), 1223 (M+24, 55%), 1224 (M+25, 88%), 1225 (M+26, 46%), 1226 (M+27, 40%), 1227 (M+28, 20%), 1228 (M+29, 15%).

EXAMPLE 6

7-triethylsilyl-13-O-[(4S,5R)-N-benzoyl-2,2-dimethyl-4-phenyl-1,3-oxazolidin-5-carbonyl]-baccatin (Compound of formula IV: =single bond; R$_1$=Ph; R$_4$,R$_5$=CH$_3$;

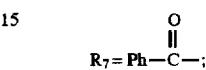

R$_8$=CH$_3$—CO; R$_9$=(CH$_3$—CH$_2$—)$_3$Si—)

A solution of 7-triethylsilyl baccatin III (Compound III: R$_8$=CH$_3$—CO—; R$_9$=(CH$_3$—CH$_2$—)$_3$Si—) (25.2 mg, 0.036 mmol) and t-butyl [(4S,5R)-N-benzoyl-2,2-dimethyl-4-phenyl-1,3-oxazolidin-5-yl] thiocarboxylate (Compound II: =single bond; R$_1$=Ph; R$_2$=Ph—CO—; R$_4$,R$_5$=CH$_3$; R$_6$=t-butyl; R$_7$=Ph—CO) (50.1 mg, 0.126 mmol) in THF (0.72 ml) at 0° C. under argon, with stirring, was treated with a freshly prepared 0.6M solution of lithium hexamethyldisilazide in THF-hexanes 62:38 (0.120 ml, 0.072 mmol). After 24 h stirring at 0° C., the mixture was quenched with a saturated NH$_4$Cl aqueous solution (2 ml). The aqueous phase was extracted with ethyl ether (3×3 ml), and the combined organic extracts were dried (Na$_2$SO$_4$) and evaporated. The crude product was purified by flash chromatography (hexanes-ethyl acetate 65:35) to give the pure title compound (27.5 mg, 75%).

[α]$_D^{25}$=−31.9° (c 1.0 in chloroform)

$^1$H-NMR (CDCl$_3$) δ=0.59 (6H, q, J=7.90 Hz, CH$_2$Si), 0.94 (9H, t, J=7.90 Hz, Me [TES]), 1.21 (3H, s, Me), 1.27 (3H, s, Me), 1.67 (3H, s, Me), 1.88 (3H, s, Me), 1.94 (3H, s, Me), 2.01 (3H, s, Me), 2.09 (3H, s, OCOMe), 2.21 (3H, s, OCOMe), 1.95–2.2 (1H, m, C6-H), 2.22–2.45 (2H, m, C14-H), 2.40–2.60 (1H, m, C6-H), 3.78 (1H, d, J=6.87 Hz, C3-H), 4.10 (1H, d, J=8.34 Hz, C20-H), 4.25 (1H, d, J=8.34 Hz, C20-H), 4.48 (1H, dd, J=6.55, 10.17 Hz, C7-H), 4.57 (1H, d, J=6.66 Hz, C2'-H), 4.89 (1H, br. d, J=9.17 Hz, C5-H), 5.28 (1H, d, J=6.66 Hz, C3'-H), 5.65 (1H, d, J=6.87 Hz, C2-H), 6.25 (1H, br. t, J=8.59 Hz, C13-H), 6.47 (1H, s, C10-H), 6.90–7.00 (2H, m, Ar—H), 7.10–7.30 (8H, m, Ar—H), 7.40–7.70 (3H, m, Ar—H), 8.02 (2H, d, J=8.21 Hz, Ar—H).

$^{13}$C NMR (CDCl$_3$) selected peaks δ=5.17, 6.64, 9.92, 14.22, 20.78, 21.01, 21.55, 25.33, 26.19, 26.36, 29.58, 35.19, 36.99, 43.12, 46.65, 58.23, 65.92, 71.63, 72.00, 74.80, 78.90, 80.69, 81.18, 84.03, 98.18, 126.06, 126.82, 127.77, 127.98, 128.46, 128.63, 129.09, 129.38, 129.95, 133.64, 133.73, 137.38, 138.74, 139.85, 166.94, 169.06, 169.16, 169.80, 201.55.

MS (FAB+): 1006 (M−1, 13%), 1007 (M, 13%), 1008 (M+H+, 29%), 1009 (M+2, 17%), 1010 (M+3, 4%), 1028 (M+21, 13%), 1029 (M+22, 12%), 1030 (M+Na+, 100%), 1031 (M+24, 716), 1032 (M+25, 27%), 1033 (M+26, 8%).

EXAMPLE 7

10-deacetyl taxol (Compound of formula I: R$_1$=Ph; R$_2$=COPh; R$_3$=H)

A solution of 7,10-di(2,2,2-trichloroethyloxycarbonyl)-10-deacetyl-13-O-[(4S,5R)-2,4-diphenyl-4,5- dihydrooxazole-5-carbonyl]-baccatin (Compound IV: ---=double bond; $R_1$=Ph; $R_5$=Ph; $R_8,R_9$=CCl$_3$—CH$_2$—OCO—) (30 mg, 0.026 mmol) in ethanol (1 ml) and 0.1N HCl (0.5 ml) was heated at about 95° C. for 2 hours. The reaction mixture was cooled, quenched cautiously with saturated aqueous sodium hydrogencarbonate, and extracted with dichloromethane (x 2), washed with water, dried over Na$_2$SO$_4$ and concentrated to give crude 7,10-di(2,2,2-trichloroethyloxycarbonyl)-10-deacetyl taxol (23 mg, 75% yield). Treatment with methanol (1 ml), acetic acid (1 ml) and powdered zinc (30 mg) at 60° C. for 1 h yielded the title compound (13 mg, 80% yield).

EXAMPLE 8

Taxol (Compound of formula I: $R_1$=Ph; $R_2$=COPh; $R_3$=Ac)

A solution of 7-triethylsilyl-13-O-[(4S,5R)-2,4-diphenyl-4,5-dihydrooxazole-5-carbonyl]-baccatin (Compound IV: ---=double bond; $R_1$=Ph; $R_5$=Ph; $R_9$=—COCH$_3$; $R_9$=(CH$_3$—CH$_2$)$_3$Si—)) (360 mg, 0.378 mmol) in 0.04N HCl in methanol:water [1.5:1 (v:v)] (40 ml) was stirred at 60° C. for 1 hour, and at 80° C. for 2.5 h. The mixture was cooled to room temperature, and a saturated NaHCO$_3$ aqueous solution (8 ml) was added (final pH=7.5). The resulting mixture was stirred at room temperature for 16 hours. Methanol (ca. 24 ml) was evaporated under vacuum (0.1 mmHg) at room temperature; the resulting aqueous mixture was then extracted with dichloromethane (3×10 ml). The organic extracts were dried (Na$_2$SO$_4$) and evaporated. The crude product was flash-chromatographed (hexanes: EtOAc 1:1) to give pure title product (259 mg, 80%).

$^1$H-NMR (CDCl$_3$) δ=1.14 (3H, s, Me), 1.25 (3H, s, Me), 1.68 (3H, s, Me), 1.79 (3H, s, Me), 2.23 (3H, s, OCOMe), 2.38 (3H, s, OCOMe), 2.35–2.40 (2H, m, C6-H), 2.40–2.60 (2H, m, C14-H), 3.67 (1H, br.s, OH), 3.79 (1H, d, J=6.96 Hz, C3-H), 4.26 (1H, A part of an AB system, J=8.42 Hz, C20-H), 4.34 (1H, B part of an AB system, J=8.42 Hz, C20-H), 4.13–4.40 (1H, m, C7-H), 4.79 (1H, br.s, C2'-H), 4.94 (1H, dd, J=7.98, 1.5 Hz, C5-H), 5.67 (1H, d, J=6.96 Hz, C2-H), 5.78 (1H, dd, J=8.89, 2.45 Hz, C3'-H), 6.23 (1H, br. t, J=9.0 Hz, C13-H), 6.27 (1H, s, C10-H), 7.03 (1H, d, J=8.89 Hz, NH), 7.30–7.60 (11H, m, Ar—H), 7.74 (2H, d, J=7.0 Hz, Ar—H), 8.13 (2H, d, J=7.0 Hz, Ar—H).

EXAMPLE 9

10-deacetyl taxol (Compound of formula I: $R_1$=Ph; $R_2$=COPh; $R_3$=H)

A solution of 7,10-di(2,2,2-trichloroethoxycarbonyl)-10-deacetyl-13-O-[(4S, 5R)-N-benzoyl-2,2-dimethyl-4-phenyl-1,3-oxazolidin-5-carbonyl]-baccatin (Compound IV: ---=single bond; $R_1$=Ph; $R_4,R_5$=CH$_3$; $R_7$=Ph—CO—; $R_8,R_9$=CCl$_3$—CH$_2$—OCO—) (52 mg, 0.043 mmol) was treated with formic acid (1 ml) at room temperature for 4 hours. The acid was removed under vacuum and the crude material was treated with methanol (1 ml), acetic acid (1 ml) and powdered zinc (40 mg) at 60° C. for 1 h yielding the title compound (30 mg, 85% yield).

EXAMPLE 10

Taxol (Compound of formula I: $R_1$=Ph; $R_2$=COPh; $R_3$=Ac)

A solution of 7-triethylsilyl-13-O-[(4S,5R)-N-benzoyl-2,2-dimethyl-4-phenyl-1,3-oxazolidin-5-carbonyl]-baccatin (Compound IV: ---=single bond; $R_1$=Ph; $R_7$=PhCO; $R_8$=CH$_3$CO; $R_9$=(CH$_3$—CH$_2$)$_3$Si—)) (35 mg, 0.035 mmol) in ethanol (1 ml) was treated with 0.1N HCl (0.5 ml) at room temperature for 3 hours to give the title compound (23 mg, 80%).

EXAMPLE 11

Phenyl(4S,5R)-2,4-diphenyl-4,5-dihydrooxazole-5-thiocarboxylate (Compound of formula II: ---=double bond; $R_1$=Ph; $R_5$=Ph; $R_1$=Ph)

To a stirred solution of phenyl (t-butyldimethylsilyloxy) thioacetate (Compound VI: $R_{10}$=TBDMS; $R_6$=Ph) (1.572 g, 5.56 mmol) in ethyl ether (25 ml) at 0° C., under argon atmosphere a solution of di{[(1S,2S,5R)-2-isopropyl-5-methylcyclohex-1-yl)-methyl}boron bromide (Compound VII: L=from (–)menthone; X=Br) in dichloromethane (0.4M; 25 ml, 10.0 mmol), and then Et$_3$N (1.47 ml, 10.56 mmol) were added dropwise. Enolborinate was generated with concurrent formation and precipitation of Et$_3$N—HBr. After 0.5 h at 0° C., the mixture was allowed to warm to room temperature and stirred for 5 h. After this time the reaction was cooled to –78° C. and a solution of N-(trimethylsilyl)benzaldimine PhCH=N—SiMe$_3$ (1.36 g, 7.67 mmol) in a minimum volume of CH$_2$Cl$_2$ (1 ml), cooled to –78° C., was added dropwise via cannula. The resulting mixture was stirred at –78° C. for 0.5 h, then slowly warmed to –5° C. during 2 h, and stirred at –5° C. overnight. The mixture was then quenched with pH 7 phosphate buffer (23 ml), and extracted with dichloromethane (3×25 ml). The combined organic extracts were dried (Na$_2$SO$_4$) and evaporated. The crude product was dissolved in 0.25N HCl in MeOH—H$_2$O [1:1 (v:v) , 40 ml]. The mixture was diluted with dichloromethane (3.0 ml), the resulting solution was stirred at room temperature for 3 h, and then evaporated to dryness under reduced pressure. The resulting crude product was pumped in vacuum (0.1 mmHg) in a dessicator overnight over phosphorus pentoxide. The white solid residue (2.35 g, 5.56 mmol) was then dissolved in dichloromethane (9.26 ml) and treated at 0° C. with 4-dimethylaminopyridine (DMAP) (0.068 g, 0.556 mmol), triethylamine (5.57 ml, 40.0 mmol) and, after further 10 minutes, with benzoyl chloride (freshly distilled) (2.26 ml, 19.44 mmol). The mixture was stirred at 0° C. for 30 min, then diluted with EtOAc (72 ml) and quenched at 0° C. with water and ice. The organic phase was washed with saturated NaHCO$_3$ aq. solution, saturated brine, dried (Na$_2$SO$_4$), and evaporated. The crude reaction product was flash chromatographed (hexanes-ethyl ether 65:35) to give phenyl 3-benzoylamino-2-tertbutyldimethylsilyloxy-3-phenylthiopropionate (67–71% yield).

The anti-syn ratio of the mixture was determined by $^1$H-NMR analysis, by integration of the relevant peaks of the anti and syn isomers (97:3). The mixture was flash chromatographed (hexanes-isopropyl ether 50:50) to give pure anti and syn isomers. anti phenyl 3(S)-benzoylamino-2(S)-tertbutyldimethylsilyloxy-3-phenylthiopropionate:

[α]$_D^{25}$=–166.6° (c 1.29 in CHCl$_3$)

$^1$H-NMR (CDCl$_3$) δ=–0.05 (3H, s, MeSi), 0.20 (3H, s, MeSi), 1.02 (9H, s, $^t$Bu), 4.78 (1H, d, CHOSi, J=5.5 Hz), 5.52 (1H, dd, J=5.5, 7.8 Hz, CHN), 6.89 (1H, d, J=7.8, NH), 7.10–7.60 (13H, m, Ar—H), 7.70–7.90 (2H, m, Ar—H).

$^{13}$C NMR (CDCl$_3$) selected peaks δ=25.74, 38.69, 57.53, 80.17, 126.92, 128.18, 128.28, 128.43, 128.53, 129.03, 129.29, 131.62, 134.65, 137.23, 166.53, 200.83.

syn phenyl 3(R)-benzoylamino-2(S)-tertbutyldimethylsilyloxy-3-phenylthiopropionate:

$^1$H-NMR (CDCl$_3$) δ=–0.21 (3H, s, MeSi), 0.14 (3H, s, MeSi), 1.00 (9H, s, tBu), 4.60 (1H, d, CHOSi, J=2.4 Hz), 5.62 (1H, dd, J=2.4, 8.8 Hz, CHN), 7.20–7.60 (13H, m, Ar—H), 7.80–8.00 (2H, m, Ar—H).

$^{13}$C NMR (CDCl$_3$) selected peaks δ=56.52, 81.03, 166.23.

The anti:syn mixture (≧97:3) (1.92 g, 3.91 mmol) was treated with a 0.5M solution of HF in acetonitrile-H$_2$O (66:1) (62.51 ml), at 0° C., under stirring. The mixture was stirred at room temperature for 24 h. The solution was evaporated to dryness. The resulting crude product was pumped in vacuum (0.1 mmHg) in a dessicator overnight over phosphorus pentoxide. The crude phenyl 3-benzoylamino-2-hydroxy-3-phenylthiopropionate (Compound IX: R$_1$=Ph; R$_6$=Ph; R$_1$=PhCO) was washed with diethyl ether to give a white amorphous solid (1.52 g, 103.4%). The mixture (97:3) was flash chromatographed (isopropyl ether—ethyl acetate 95:5) to give analytically pure anti phenyl 3(S)-benzoylamino-2(S)-hydroxy-3-phenylthiopropionate and syn phenyl 3(R)-benzoylamino-2(S)-hydroxy-3-phenylthiopropionate.

anti phenyl 3(S)-benzoylamino-2(S)-hydroxy-3-phenylthiopropionate:

$[α]_D^{25}$=−140.23° (c 0.8 in acetone).

$^1$H-NMR (CD$_3$COCD$_3$) δ=4.90 (1H, dd, CHOH, J=5.6, 6.3 Hz), 5.65 (1H, dd, J=5.6, 8.6 Hz, CHN), 5.94 (1H, d, J=6.3, OH), 7.10–7.70 (13H, m, Ar—H), 7.80–7.90 (2H, m, Ar—H), 8.05 (1H, d, J=8.6, NH).

$^{13}$C NMR (CD$_3$COCD$_3$) selected peaks δ__=56.53, 79.10, 127.41, 127.61, 128.00, 128.28, 128.90, 129.32, 131.30, 134.69, 138.15, 139.89, 166.24, 200.39.MS(E.I.): 378 (M+1, 57%), 360, 268, 240, 222, 210, 193, 105 (1006), 91, 77.

syn phenyl 3(R)-benzoylamino-2(S)-hydroxy-3-phenylthiopropionate:

$[α]_D^{25}$=−67.0° (c 1.04 in acetone) (e.e.=34%).

$^1$H-NMR (CD$_3$COCD$_3$) δ__=4.80 (1H, d, CHOH, J=3.4 Hz), 5.70 (1H, dd, J=3.4, 8.2 Hz, CHN), 7.12–7.60 (13H, m, Ar—H), 7.90–8.01 (2H, m, Ar—H).

$^{13}$C NMR (CD$_3$COCD$_3$) selected peaks δ=56.28, 79.92.

Determination of the absolute configuration of phenyl 3(S)-benzoylamino-2(S)-hydroxy-3-phenylthioprolionate Chromatographed phenyl 3(S)-benzoylamino-2(S)-hydroxy-3-phenyl thiopropionate was saponified [a) 30% H$_2$O$_2$ (4 eq.), LiOH aq. (2 eq.), THF, 0° C., 15 h; b) Na$_2$SO$_3$, see Tetrahedron Lett. 1990, 31, 7513] to give the corresponding acid.

$^1$H-NMR (CD$_3$OD) δ=4.61 (1H, d, J=5.5, CHO), 5.52 (1H, d, J=5.5, CHN), 7.20–7.60 (8H, m, Ar—H), 7.80–7.85 (2H, m, Ar—H).

A solution of the acid in methanol was treated with a CH$_2$N$_2$ solution in ethyl ether to give the corresponding methyl ester.

$[α]_D^{25}$=+9.0° (c 1.0 in MeOH).

Reported in the literature:

$[α]_D^{20}$=+8.70 (c 1.03 in MeOH) (ref. J.Org.Chem. 1992, 57, 6387); $[α]_D^{20}$=+9.5° (c 1.01 in MeOH) (ref. J.Chem.Soc., Perkin Trans. 1, 1994, 2385).

$^1$H-NMR (CDCl$_3$) δ=3.13 (1H, d, J=6.3, OH), 3.75 (3H, s, OCH$_3$), 4.73 (1H, br. m, CHO), 5.64 (1H, dd, J=3.5, 8.6 Hz, CHN), 7.17 (1H, br. d, J=8.6, NH), 7.30–7.53 (8H, m, Ar—H), 7.81–7.84 (2H, m, Ar—H).

$^{13}$C NMR (CDCl$_3$) δ=52.6, 55.6, 73.1, 127.3, 127.7, 128.5, 128.8, 131.9, 134.3, 136.8, 167.1, 172.7.

Determination of the enantiomeric excess of phenyl 3(S)-benzoylamino-2(S)-hydroxy-3-phenylthiorropionate The % enatiomeric excess of phenyl 3(S)-benzoylamino-2(S)-hydroxy-3-phenylthiopropionate was determined by $^1$H-NMR analysis of the Mosher ester derivatives. Chromatographed compound was treated with excess (S)-(−)-α-methoxy-α-(trifluoromethyl) phenylacetic acid in dichloromethane in the presence of 1,3-dicyclohexylcarbodiimide (DCC) and catalytic 4-dimethylaminopyridine (DMAP). The Mosher derivative phenyl 3-(S)-benzoylamino-2(S)-O-[(S)-α-methoxy-α-(trifluoromethyl) phenyl]acetyl-3-phenylthiopropionate was obtained:

$^1$H-NMR (CDCl$_3$) δ=3.61 (3H, m, OMe), 5.91 (1H, dd, J=4.40, 7.82 Hz, CHN), 6.02 (1H, d, J=4.40 Hz, CHO), 6.53 (1H, d, J=7.82 Hz, NH), 7.20–7.60 (18H, m, Ar—H), 7.60–7.80 (2H, m, Ar—H).

A pure sample of phenyl 3(R)-benzoylamino-2(R)-hydroxy-3-phenylthiopropionate was obtained via the same reaction sequence, but using the boron reagent di{[(1R,2R,5S)-2-isopropyl-5-methylcyclohex-1-yl]-methyl}boron bromide derived from (+)menthone. Compound phenyl 3(R)-benzoylamino-2(R)-hydroxy-3-phenyl-thiopropionate was treated with excess (S)-(−)-α-methoxy-α-(trifluoromethyl) phenylacetic acid in dichloromethane in the presence of 1,3-dicyclohexyl carbodiimide (DCC) and catalytic 4-dimethylaminopyridine (DMAP). The Mosher derivative phenyl 3(R) -benzoylamino-2(R)-O-[(S)-α-methoxy-α-(trifluoromethyl)phenyl]acetyl-3-phenylthiopropionate was obtained:

$^1$H-NMR (CDCl$_3$) δ=3.45 (3H, m, OMe), 5.92 (1H, dd, J=5.30, 7.63 Hz, CHN), 6.03 (1H, d, J=5.30 Hz, CHO), 6.90 (1H, d, J=7.63 Hz, NH), 7.20–7.60 (18H, m, Ar—H), 7.60–7.80 (2H, m, Ar—H).

The ratio phenyl 3(S)-benzoylamino-2(S)-hydroxy-3-phenylthiopropionate:phenyl 3(R)-benzoylamino-2(R)-hydroxy-3-phenylthiopropionate was determined by integration of the relevant peaks, and was shown to be ≧97.5:2.5 (e.e.≧95%) over a series of several experiments.

Determination of the enantiomeric excess of phenyl 3(R)-benzoylamino-2(S)-hydroxy-3-lphenylthiopropionate The % enatiomeric excess of syn phenyl 3(R)-benzoylamino-2(S)-hydroxy-3-phenylthiopropionate was determined by $^1$H-NMR analysis of the Mosher ester derivatives. Chromatographed compound phenyl 3(R)-benzoylamino-2(S)-hydroxy-3-phenylthiopropionate was treated with excess (S)-(−)-α-methoxy-α-(trifluoromethyl) phenylacetic acid in dichloromethane in the presence of 1,3-dicyclohexyl carbodiimide (DCC) and catalytic 4-dimethylaminopyridine (DMAP). The Mosher derivative phenyl 3(R)-benzoylamino-2(S)-O-[(S)-α-methoxy-α-(trifluoromethyl) phenyl]acetyl-3-phenylthiopropionate was obtained:

$^1$H-NMR (CDCl$_3$) δ=3.52 (3H, m, OMe), 5.85 (1H, d, J=2.25 Hz, CHO), 6.06 (1H, dd, J=2.25, 9.25 Hz, CHN), 6.94 (1H, d, J=9.25 Hz, NH), 7.10–7.60 (18H, m, Ar—H), 7.60–7.80 (2H, m, Ar—H).

A pure sample of phenyl 3(S)-benzoylamino-2(R)-hydroxy-3-phenylthiopropionate was obtained via the same reaction sequence, but using the boron reagent di{((1R,2R,5S)-2-isopropyl-5-methylcyclohex-1-yl]-methyl}boron bromide, derived from (+)menthone. Compound phenyl 3(S)-benzoylamino-2(R)-hydroxy-3-phenylthiopropionate was treated with excess (S)-(−)-α-methoxy-α-(trifluoromethyl) phenylacetic acid in dichloromethane in the presence of 1,3-dicyclohexylcarbodiimide (DCC) and catalytic 4-dimethylaminopyridine (DMAP). The Mosher derivative phenyl 3(S)-benzoylamino-2(R)-O-[(S)-α-methoxy-α-(trifluoromethyl)phenyl]acetyl-3-phenylthiopropionate was obtained:

¹H-NMR (CDCl₃) δ=3.41 (3H, m, OMe), 5.81 (1H, d, J=2.21, CHO), 6.11 (1H, dd, J=2.21, 9.22 Hz, CHN), 6.90 (1H, d, J=9.22 Hz, NH), 7.10–7.60 (18H, m, Ar—H), 7.60–7.80 (2H, m, Ar—H).

The ratio phenyl 3(R)-benzoylamino-2(S)-hydroxy-3-phenylthiopropionate:phenyl 3(S)-benzoylamino-2(R)-hydroxy-3-phenylthiopropionate was determined by integration of the relevant peaks, and was shown to be 67:33 (e.e.=34%) over a series of several experiments.

A solution of phenyl 3-benzoylamino-2-hydroxy-3-phenylthiopropionate (2S,3S:2S,3R ratio=≧97:3, crude, without chromatography; 1.520 g, 3.89 mmol) in chloroform (40.20 ml) was treated with thionyl chloride (1.47 ml, 20.13 nmol), and stirred at 45° C. for 3–4 h. The solvent was removed in vacuum, and the crude product was dissolved in 1,2-dichloroethane (20 ml) in the presence of 3 Å-molecular sieves.

The resulting mixture was refluxed (100° C.) for 5 h. The solution was then filtered, dried (Na₂SO₄), and evaporated to give a crude product, which was purified by flash-chromatography (methylene chloride: hexanes 88:12) to give pure phenyl (4S,5R)-2,4-diphenyl-4,5-dihydrooxazole-5-thiocarboxylate in 65% yield.

$[\alpha]_D^{25}$=+91.28° (c 0.8 in chloroform)

¹H-NMR (CDCl₃) δ=5.06 (1H, d, CHN, J=5.6Hz), 5.55 (1H, d, J=5.61 Hz, CHO), 7.20–7.60 (13H, m, Ar—H), 8.10–8.30 (2H, m, Ar—H).

¹³C NMR (CDCl₃) selected peaks δ=75.48, 89.10, 126.41, 128.01, 128.60, 128.86, 129.31, 129.72, 132.15, 134.65. MS(E.I.): 360 (M+1, 57%), 250, 222, 193, 119, 109, 91 (100%), 77, 65.

EXAMPLE 12

Phenyl (tertbutyldimethylsilyloxy)thioacetate (Compound of formula VI: R₁₀=TBDMS; R₁=Ph)

Methyl glygolate (1.90 ml, 2.20 g, 24.5 mmol) was added to a suspension of tertbutyldimethylsilylchloride (4.43 g, 29.4 mmol) and imidazole (4.17 9, 61.25 mmol) in dry dimethylformamide (DMF) (4.9 ml) at 0° C., under stirring. After 90 min stirring at RT, water (60 ml) was added, and the resulting mixture was extracted with ethyl ether (3×35 ml). The organic phases were combined, washed with water (3×35 ml), dried (Na₂SO₄) and evaporated to give methyl (tertbutyldimethylsilyloxy)acetate (5.0 g, 100%).

¹H-NMR (CDCl₃) δ=0.12 (6H, s, Me), 0.93 (9H, s, tBu), 3.75 (3H, s, OMe), 4.26 (2H, s, CH₂).

A solution of AlMe3 (2.0M in hexanes, 12.25 ml, 24.5 mmol) in methylene chloride (49 ml) was treated at 0° C. with PhSH (2.5 ml, 24.5 mmol). After 20 min at 0°, a solution of methyl (tertbutyldimethylsilyloxy)acetate (2.5 g, 12.25 mmol) in methylene chloride (6.125 ml) was added at 0° C. The mixture was stirred at RT for 0.5 h, then quenched with NH4Cl saturated aqueous solution (12 ml), filtered through celite, washing the celite cake with methylene chloride. The organic phase was washed with 5% aqueous NaOH, saturated brine, dried (Na₂SO₄) and evaporated to give a crude mixture which was purified by flash chromatography (hexanes-ethyl ether 95:5) to afford pure title compound (2.74 g, 79w).

¹H-NMR (CDCl₃) δ=0.20 (6H, s, Me), 1.01 (9H, s, ᵗBu), 4.38 (2H, s, CH₂), 7.43 (5H, m, Ar—H).

EXAMPLE 13

Phenyl 3(S)-benzoylamino-2(S)-hydroxy-3-phenylthiopropionate (Compound of formula IX: R₁,R₆=Ph; R₇=PhCO)

To a stirred solution of phenyl (1-ethoxyethoxy) thioacetate (0.09 g, 0.37 mmol) in ethyl ether (1.5 ml) at 0° C., under argon, a solution of di{[(1S,2S,5R)-2-isopropyl-5-methylcyclohex-1-yl]-methyl}boron bromide in dichloromethane (0.4M; 1.5 ml, 0.6 mmol), and then Et₂N (0.09 ml, 0.630 mmol) were added dropwise. Enolborinate was generated with concurrent formation and precipitation of Et₃N—HBr. After 5 h at 0° C., the mixture was cooled to −78° C. and N-(trimethylsilyl)benzaldimine (0.185 g, 1.04 mmol) was added dropwise. The resulting mixture was stirred at −78° C. for 0.5 h, then slowly warmed to −5° C. during 2 h, and stirred at −5° C. overnight.

The mixture was then quenched with ph 7 phosphate buffer, and extracted several times with dichloromethane. The organic phase was evaporated to give a residue which was dissolved in 1:1 (v:v) MeOH:1.0N aqueous HCl and stirred at room temperature for 1 h. The resulting solution was evaporated to dryness and pumped (0.1 mmHg). The crude residue was dissolved in 1N aqueous HCl and the aqueous phase was washed several times with ethyl ether. The aqueous phase was evaporated to dryness and pumped (0.1 mmHg). The resulting crude mixture was then dissolved in 1:1 (v:v) dichloromethane: water and treated at room temperature with benzoyl chloride (1.5 mol.equiv.) and then with solid NaHCO₃ (2.5 mol. equiv., added in 0.5 mol.equiv. portions). The reaction was followed by t.l.c., and after 1 h stirring at room temperature, the mixture was extracted with dichloromethane. The organic extracts were dried is (Na₂SO₄) and evaporated. The crude compound was purified by flash chromatography (ethyl ether : CH₂Cl₂ 60:40) to give pure title compound (anti:syn>99:1) in 50% overall yield. The % e.e. (enantiomeric excess), determined by ¹H-NMR analysis of the Mosher ester derivatives, was 85 (see the relevant section above for procedure).

EXAMPLE 14

Phenyl (1-ethoxyethoxy)thioacetate
(Compound of formula VI:

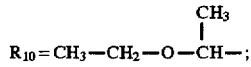

R₆=Ph)

A solution of methyl glycolate (0.193 g, 2.15 mmol) in THF (21 ml) was treated with ethylvinyl ether (EVE) (1.03 ml, 10.7 mmol) and a catalytic amount of p-TsOH (41 mg). After stirring for 15 min at 0° C., the mixture was diluted with ethyl ether, washed with saturated NaHCO₃ aqueous solution, brine, dried (Na₂SO₄) and evaporated to give methyl (1-ethoxyethoxy)acetate (0.306 g, 87%).

¹H-NMR (CDCl₃) δ=1.20 (3H, t, J=7.14 Hz, Me), 1.37 (3H, d, J=5.95 Hz, Me), 3.60 (2H, m, CH₂), 3.78 (3H, s, COOMe), 4.16 (2H, S, CH₂CO), 4.85 (1H, q, J=5.95 Hz, CH).

A solution of AlMe₃ (2.0M in hexanes, 3.2 ml, 6.4 mmol) in methylene chloride (12.8 ml) was treated at 0° C. with PhSH (0.658 ml, 6.4 mmol). After 20 min at 0°, a solution of methyl (1-ethoxyethoxy)acetate (0.527 g, 3.2 nmol) in methylene chloride (1.6 ml) was added at 0° C. The mixture was stirred at RT for 20 min, then diluted with ethyl ether, washed with 1N aqueous HCl, dried (Na₂SO₄) and evaporated. The crude product was purified by flash chromatography (hexanes-ethyl ether 50:50) to afford pure phenyl (hydroxy)thioacetate (0.3 g, 40%).

$^1$H-NMR (CDCl$_3$) δ=4.43 (2H, s, CH$_2$CO), 7.45 (5H, m, Ar—H).

A solution of phenyl (hydroxy)thioacetate (0.107 g, 0.64 mmol) in THF (6.4 ml) was treated with ethylvinyl ether (EVE) (0.307 ml, 3.2 mmol) and a catalytic amount of p-TsOH (12 mg). After stirring for 15 min at 0° C., the mixture was diluted with ethyl ether, washed with saturated NaHCO$_3$ aqueous solution, brine, dried (Na$_2$SO$_4$) and evaporated to give title compound (0.266 g, 86%).

$^1$H-NMR (CDCl$_3$) δ=1.22 (3H, t, J=6.57 Hz, Me), 1.40 (3H, d, J=4.82 Hz, Me), 3.65 (2H, m, CH$_2$), 4.30 (2H, s, CH$_2$CO), 4.90 (1H, q, J=4.82 Hz, CH), 7.40 (5H, s, Ar—H).

EXAMPLE 15

Phenyl 3(S)-benzoylamino-2(S)-hydroxy-3-phenylthiopropionate (Compound of formula IX: R$_1$=Ph; R$_6$=Ph, R$_7$=PhCO)

To a stirred solution of phenyl (trimethylsilyloxy) thioacetate (0.212 g, 0.881 mmol) in ethyl ether (4 ml) at 0° C., under argon, a solution of di{[(1S,2S,5R)-2-isopropyl-5-methylcyclohex-1-yl]-methyl}boron bromide in dichloromethane (0.4M; 3.96 ml, 1.585 mmol), and then Et$_3$N (0.233 ml, 1.673 mmol) were added dropwise. Enolborinate was generated with concurrent formation and precipitation of Et$_3$N—HBr. After 5 h at 0° C., the mixture was cooled to −78° C. and N-(trimethylsilyl)benzaldimine (0.390 g, 2.202 mmol) was added dropwise. The resulting mixture was stirred at −78° C. for 0.5 h, then slowly warmed to −5° C. during 2 h, and stirred at −5° C. overnight. The mixture was then quenched with pH 7 phosphate buffer, and extracted several times with dichloromethane. The organic phase was evaporated to give a residue which was dissolved in 1:1 (v:v) MeOH:1.0N aqueous HCl and stirred at room temperature for 1 h. The resulting solution was evaporated to dryness and pumped (0.1 mmHg). The crude residue was dissolved in 1N aqueous HCl and the aqueous phase was washed several times with ethyl ether. The aqueous phase was evaporated to dryness and pumped (0.1 mmHg). The resulting crude mixture was then dissolved in 1:1 (v:v) dichloromethane:water and treated at room temperature with benzoyl chloride (1.5 mol.equiv.) and then with solid NaHCO$_3$ (2.5 mol. equiv., added in 0.5 mol.equiv. portions). The reaction was followed by t.l.c., and after 1 h stirring at room temperature, the mixture was extracted with dichloromethane. The organic extracts were dried (Na$_2$SO$_4$) and evaporated. The crude compound was purified by flash chromatography (ethyl ether:dichloromethane 60:40) to give the pure title compound in 50% overall yield. The % e.e. (enantiomeric excess) of phenyl 3(S)-benzoylamino-2(S)-hydroxy-3-phenylthiopropionate was determined by $^1$H-NMR analysis of the Mosher ester derivatives (see the relevant section above for the procedure), and shown to be 88.

EXAMPLE 16

Phenyl (trimethylsilyloxy)thioacetate

A solution of phenyl (hydroxy)thioacetate (0.237 g, 1.41 mmol) in THF (14.0 ml) was treated with trimethylsilyl chloride (0.643 ml, 5.07 mmol) and triethylamine (0.726 ml, 5.21 mmol) at room temperature. After stirring for 2 h at RT, the mixture was diluted with ethyl ether, washed with pH 7 phosphate buffer, dried (Na$_2$SO$_4$) and evaporated to give phenyl (trimethylsilyloxy)thioacetate (0.2315 g, 93%).

$^1$H-NMR (CDCl$_3$) δ=0.22 (9H, s, Me—Si), 4.31 (2H, s, CH$_2$CO)

EXAMPLE 17

'Butyl [(4S,5R)-N-benzoyl-2,2-dimethyl-4-phenyl-1,3-oxazolidin-5-yl]thiocarboxylate (Compound of formula II: ==single bond; R$_1$=Ph; R$_4$,R$_5$=CH$_3$; R$_6$='Bu; R$_1$=PhCO)

To a stirred solution of tertbutyl (benzoxy)thioacetate (Compound VI: R$_6$α'Bu; R$_{10}$=PhCO) (0.184 g, 0.730 mmol) in ethyl ether (3.2 ml) at −25° C., under argon, a solution of di{[(1R,2R,5S)-2-isopropyl-5-methylcyclohex-1-yl]-methyl}boron bromide (Compound VII: L=from(+)-menthone; X=Br) in dichloromethane (0.4M; 3.2 ml, 1.28 mmol), and then Et$_3$N (0.188 ml, 1.35 mmol) were added dropwise. Enolborinate was generated with concurrent formation and precipitation of Et$_3$N—HBr. After 7.0 h at −25° C., the mixture was cooled to −78° C. and N-(trimethylsilyl)benzaldimine (Compound VIII: R$_1$=Ph; Z=(CH$_3$)$_3$Si)) (1.46 mmol) was added dropwise. The resulting mixture was stirred at −78° C. for 0.5 h, then slowly warmed to −5° C. during 2 h, and stirred at −5° C. overnight. The mixture was then quenched with pH 6 phosphate buffer, and extracted several times with dichloromethane. The organic phase was evaporated to give a residue which was dissolved in 1:1 (v:v) MeOH: 1N aqueous HCl (24.0 ml) and stirred at room temperature for 1 h. The resulting solution was evaporated to dryness and pumped (0.1 mmHg). The white solid residue was washed with dry ethyl ether (3×10 ml), removing the ethyl ether phase by centrifugation and decantation. The white solid residue was then dissolved in MeOH (10.0 ml) and pH 8 phosphate buffer (10.0 ml) at RT, and stirred at RT for 1 h. The pH was adjusted to 7 with dil. (0.1M) aqueous HCl, the mixture was concentrated in order to remove most of the methanol, and the aqueous phase was extracted with CH$_2$Cl$_2$ (3×10 ml). The organic phase was dried (Na$_2$SO$_4$) and evaporated to give practically pure tertbutyl 3(S)-benzoylamino-2(R)-hydroxy-3-phenylthiopropionate (0.139 g, 53%). In addition, 19.7 mg (7.5%) of the same compound were obtained via flash chromatography (hexanes-acetone 70:30) of the crude mixture contained in the ethyl ether phase, used to wash the white solid residue (see above). Total yield=60.5%. The product was flash chromatographed (pentanes-ethyl ether 50:50) to give analytically pure tert-butyl 3(S)-benzoylamino-2(R)-hydroxy-3-phenylthiopropionate (Compound IX: R$_1$=Ph; R$_6$=tBu; R$_7$=PhCO):

[α]$_D^{25}$=−12.2° (c 1.69 in CHCl$_3$)

$^1$H-NMR (CDCl$_3$) δ=1.45 (9H, s, 'Bu), 3.85 (1H, br.s, OH), 4.57 (1H, br.d, CHO), 5.70 (1H, dd, J=2.5, 8.7 Hz, CHN), 7.14 (1H, d, J=8.7, NH), 7.20–7.60 (8H, m, Ar—H), 7.70–7.90 (2H, m, Ar—H).

$^{13}$C NMR (CDCl$_3$) δ=29.60, 38.79, 56.42, 79.62, 126.87, 127.02, 127.77, 128.57, 131.61, 138.27, 166.94, 202.16, MS(E.I.) : 358 (M+1), 268, 250, 222, 210, 193, 122, 105, 91, 77.

Determination of the absolute configuration of tertbutyl 3(S)-benzoylamino-2(R)-hydroxy-3-phenylthiopropionate Chromatographed tertbutyl 3(S)-benzoylamino-2(R)-hydroxy-3-phenylthiopropionate was saponified |a) 30% H$_2$O$_2$ (4 eq.), LiOH aq. (8 eq.), THF, 0° C., 15 h; b) Na$_2$SO$_3$, see JACS 1989, 111, 5493; Tetrahedron Lett. 1990, 31, 7513] to give the corresponding acid. $^1$H-NMR (CD$_3$OD) δ=4.55 (1H, d, J=3.0, CHO), 5.62 (1H, d, J=3.0, CHN), 7.20–7.60 (8H, m, Ar—H), 7.81–7.84 (2H, m, Ar—H). A solution of the acid in methanol was treated with a CH$_2$N$_2$ solution in ethyl ether to give the corresponding methyl ester.

$[\alpha]_D^{25}=-47.6°$ (c 1.15 in MeOH).

Reported in the literature:

$[\alpha]_D^{25}=-49.6°$ (MeOH) (ref. JACS 1971, 93, 2325);

$[\alpha]_D^{26}=-48.0°$ (c 0.92 in MeOH) (ref. JOC 1986, 51, 46);

$[\alpha]_D^{24}=-48.0°$ (c 1.0 in MeOH) (ref. JOC 1990, 55, 1957);

$[\alpha]_D^{20}=-8.4°$ (c 0.98 in MeOH) (ref. J.Chem.Soc., Perkin Trans. 1, 1994, 2385).

$^1$H-NMR (CDCl$_3$) δ=3.33 (1H, d, J=3.9, OH), 3.85 (3H, s, OCH$_3$), 4.65 (1H, dd, J=3.9, 2.1, CHO), 5.76 (1H, dd, J=2.1, 9.0 Hz, CHN), 7.00 (1H, br. d, J=9.0, NH), 7.30–7.54 (8H, m, Ar—H) 7.77–7.79 (2H, m, Ar—H).

$^{13}$C NMR (CDCl$_3$) δ=53.2, 55.0, 73.3, 127.0, 127.1, 128.0, 128.7, 128.8, 131.7, 134.3, 138.9, 166.9, 173.4.

Determination of the syn-anti ratio of tertbutyl 3(S)-benzoylamino-2(R)-hydroxy-3--phenylthiopropionate The syn-anti ratio of crude tertbutyl 3(S)-benzoylamino-2(R)-hydroxy-3-phenylthiopropionate (not chromatographed) was determined by $^1$H-NMR analysis, by integration of the relevant peaks of the syn and anti isomers (≧96:4). A pure sample of the anti isomer was obtained using a different reaction scheme.

$^1$H-NMR of the anti isomer (CDCl$_3$) δ=1.45 (9H, s, $^t$Bu), 3.53 (1H, br.s, OH), 4.68 (1H, br.d, CHO), 5.63 (1H, dd, J=3.3, 8.4 Hz, CHN), 7.17 (1H, d, J=8.4, NH), 7.20–7.60 (8H, m, Ar—H), 7.80–7.90 (2H, m, Ar—H).

Determination of the enantiomeric excess of tertbutyl 3(S)-benzoylamino-2(R)-hydroxy-3-Phenylthiopropionate The % enatiomeric excess of tertbutyl 3(S)-benzoylamino-2(R)-hydroxy-3-phenylthiopropionate was determined by $^1$H-NMR analysis of the Mosher ester derivatives. Chromatographed tertbutyl 3(S)-benzoylamino-2(R)-hydroxy-3-phenylthiopropionate was treated with excess (S)-(–)-α-methoxy-α-(trifluoromethyl)-phenylacetic acid in dichloromethane in the presence of 1,3-dicyclohexylcarbodiimide (DCC) and catalytic 4-dimethylaminopyridine (DMAP). The Mosher derivative tertbutyl 3(S)-benzoylamino-2(R)-O-[(S)-α-methoxy-α-(trifluoromethyl)phenyl]acetyl-3-phenylthiopropionate was obtained:

$^1$H-NMR (CDCl$_3$) δ=1.42 (9H, s, $^t$Bu), 3.38 (3H, m, OMe), 5.56 (1H, d, J=2.21, CHO), 6.03 (1H, dd, J=2.21, 8.94 Hz, CHN), 6.85 (1H, d, J=8.94, NH), 7.20–7.60 (m, Ar—H), 7.70 (m, Ar—H).

A pure sample of tertbutyl 3(R)-benzoylamino-2(S)-hydroxy-3-phenylthiopropionate was obtained via the same reaction sequence, but using the boron reagent di{[(1S,2S,5R)-2-isopropyl-5-methylcyclohex-1-yl]-methyl}boron bromide, derived from (–)menthone. Compound tertbutyl 3(R)-benzoylamino-2(S)-hydroxy-3-phenylthiopropionate was treated with excess (S)-(–)-α-methoxy-α-(trifluoromethyl) phenylacetic acid in dichloromethane in the presence of 1,3-dicyclohexylcarbodiimide (DCC) and catalytic 4-dimethylaminopyridine (DMAP). The Mosher derivative tertbutyl 3(R)-benzoylamino-2(S)-O-[(S)-α-methoxy-α-trifluoromethyl)phenyl]acetyl-3-phenylthiopropionate was obtained:

$^1$H-NMR (CDCl$_3$) δ=1.43 (9H, 5, $^t$Bu), 3.51 (3H, m, OMe), 5.61 (1H, d, J=2.31, CHO), 5.96 (1H, dd, J=2.31, 9.21 Hz, CHN), 6.59 (1H, d, J=9.21, NH), 7.20–7.60 (m, Ar—H), 7.70 (m, Ar—H).

The ratio tertbutyl 3(S)-benzoylamino-2(R)-hydroxy-3-phenylthiopropionate:tertbutyl 3(R)-benzoylamino-2(S)-hydroxy-3-phenylthiopropionate was determined by integration of the relevant peaks, and was shown to be ≧98:2 (e.e. >96%) over a series of several experiments.

Determination of the absolute configuration via the Mosher method (ref. JACS 1991, 113, 4092; Bull.Chem. Soc.Jpn. 1994, 67, 2600) is in accord with the determination via chemical correlation (see above). The CHO stereocentre is R or S depending on the different chemical shift of CHN proton:

δ CHN (tertbutyl 3(S)-benzoylamino-2(R)-O-[(S)-α-methoxy-α-(trifluoromethyl)phenyl] acetyl-3-phenylthiopropionate)=6.03;

δ CHN (tertbutyl 3(R)-benzoylamino-2(S)-O-[(S)-α-methoxy-α-(trifluoromethyl)phenyl] acetyl-3-phenylthiopropionate)=5.96, shifted upfield due to the diamagnetic effect of the Mosher ester phenyl ring.

A solution of tertbutyl 3(S) -benzoylamino-2(R) -methyl-3-phenylthiopropionate (not chromatographed, containing ≦4% of the anti isomer), (186 mg, 0.5203 mmol) in toluene (5.2 ml) was treated with pyridinium tosylate (13 mg) and freshly distilled 2-methoxypropene (0.98 ml). The mixture was stirred at RT for 5 min, and at 80° C. for 75 min. After dilution with ethyl acetate (15 ml), the organic phase was washed with aqueous NaHCO$_3$ sat. solution (5 ml), brine (2×5 ml), dried (Na$_2$SO$_4$)$_1$ and evaporated to give a crude mixture. Purification via flash chromatography (hexanes-acetone 90:10) gave pure tertbutyl [(4S,5R)-N-benzoyl-2,2-dimethyl-4-phenyl-1,3-oxazolidin-5-yl]thiocarboxylate (186 mg, 90%).

$[\alpha]_D^{25}=+39.4°$ (c 1.0 in CHCl$_3$)

$^1$H-NMR (CDCl$_3$) δ=1.52 (9H, s, $^t$-Bu), 1.91 (3H, s, Me), 1.96 (3H, s, Me), 4.50 (1H, d, J=5.65, CHO), 5.20 (1H, d, J=5.65 Hz, CHN), 6.90–7.30 (10H, m, Ar—H).

$^{13}$C NMR (CDCl$_3$) δ=25.73, 26.27, 29.59, 48.13, 56.37, 87.35, 126.10, 126.66, 127.58, 127.98, 128.23, 128.38, 129.25, 131.57, 137.47, 138.89, 168.00, 198.72.

MS(E.I.): 398 (M+1, 44%), 382, 340, 292, 280 (100%), 250, 210, 162, 146, 105, 91, 77.

EXAMPLE 18

Tertbutyl (benzoxy)thioacetate (Compound of formula VI: R$_6$=$^t$Bu; R$_{10}$=PhCO)

A solution of AlMe$_3$ (2.0M in hexanes, 30.4 ml, 60.8 mmol) in methylene chloride (65 ml) was treated at 0° C. with $^t$BuSH (6.85 ml, 60.8 mmol). After 20 min at 0°, a solution of methyl glycolate (0.786 ml, 10.1 mmol) in methylene chloride (15.2 ml) was added at −10° C. The mixture was stirred at 0° C. for 48 hr., then quenched with NH$_4$Cl saturated aqueous solution (30 ml), filtered through celite, washing the celite cake with methylene chloride. The organic phase was dried (Na$_2$SO$_4$) and evaporated to give a crude mixture which was purified by flash chromatography (hexanes-ethyl ether 7:3) to afford pure tertbutyl (hydroxy) thioacetate (0.72 g, 48%). A solution of the above mentioned compound (0.72 g, 4.88 mmol) in methylene chloride (32.5 ml) was treated with DMAP (0.06 g, 0.488 mmol), triethylamine (1.0 ml, 7.318 mmol) and benzoyl chloride (0.736 ml, 6.342 mmol) at 0° C., under stirring. After 30 min at 0° C., a saturated aqueous NH$_4$Cl solution (10 ml) was added, and the organic phase was separated, dried (Na$_2$SO$_4$) and evaporated to give a crude compound, which was purified by flash chromatography (hexanes-ethyl ether 94:6) to afford pure tertbutyl (benzoxy)thioacetate (1.04 g, 85%).

$^1$H-NMR (CDCl$_3$) δ=1.52 (9H, s, $^t$Bu), 4.89 (2H, S, CH$_2$), 7.45–7.65 (4H, m, Ar—H), 8.10–8.18 (2H, m, Ar—H).

EXAMPLE 19

Di{[(1S,2S, 5R)-2-isopropyl-5-methylcyclohex-1-yl] -methyl}boron bromide (Compound of formula VII: L=from(−)menthone; X=Br)

A solution of (−)-(2S,5R)-2-isopropyl-5-methyl-1-methylene cyclohexane (98%, 5.5 g, 35.48 mmol) obtained from (−)-menthone as described in literature (ref. J.Org.Chem. 1992, 57, 5173; Angew.Chem.Int., Ed.Engl., 1993, 32, 1618; Tetrahedron Lett. 1994, 35, 4623) in freshly distilled dichloromethane (17.0 ml) was treated with $BrBH_2$-$SMe_2$ (95%, Aldrich)(1.99 ml, 17.68 mmol) at 0° C., under argon, with stirring. The reaction mixture was stirred at room temperature overnight. The solvent dichloromethane and dimethylsulfide liberated during hydroboralion were removed under vacuum (0.1 mmHg) and the residue (a thick liquid or a low melting solid) was dissolved in dry diethyl ether (8.2 ml) under argon at RT. The solution was cannulated off of a small amount of insoluble residue (white powder) into another flask. The solution was cooled to −50° C. and left to crystallize for 1.0 h. The solvent was removed via double-tipped needle (cannula) under argon at −50° C. The remaining white crystals were then dissolved in dry diethyl ether (5.0 ml) at RT and the resulting solution was cooled (SLOWLY) to −40° C. and after 1.0 h the mother liquor was removed via cannula from the crystals formed. The crystals were redissolved in dry ether (5.5 ml) at RT. The solution was cooled (SLOWLY) to −30° C. and after 1.0 h the mother liquor was removed via cannula from the crystals formed. The crystals (containing 1 eq. of diethyl ether per eq. of boron atom) were weighed under argon (3.02 g, 36%). The ratio between the diastereoisomers was determined by decomposition with hydrogen peroxide and VPC analysis (OV-1 column, 70°–150° C.) of alcohol (1S,2S,5R) -1-(hydroxymethyl)-2-isopropyl-5-methylcyclohexane and (1R,2S,5R)-1-(hydroxymethyl)-2-isopropyl-5-methylcyclohexane (≧100:1).

$^{11}B$ NMR [200 MHz, $CDCl_3$, 25° C., ppm relative to $BF_3$-$Et_2O$ (0.0)]:

δ=78.83.

Methanolysis gave X=OMe: $^{11}B$ NMR [200 MHz, $CDCl_3$, 25° C., ppm relative to $BF_3$-$Et_2O$ (0.0)]: δ=55.05.

$^{13}C$ NMR ($CDCl_3$) δ=53.30 ($OCH_3$), 48.39, 42.26, 35.85, 31.38, 29.57, 26.17, 24.54, 22.74, 21.41, 20.69, 16.3 (broad, C-B).

Treatment of X=OMe with $HOCH_2CH_2NH_2$ in $Et_2O$ gave X=$OCH_2CH_2NH_2$: $^{13}C$ NMR ($CDCl_3$) δ=65.52 ($OCH_2$), 48.86, 42.62 ($CH_2NH_2$), 41.93, 35.98, 31.82, 29.41, 26.24, 24.51, 22.76, 21.45, 20.71, 16 (broad, C-B).

Anal. for $C_{24}H_{48}BNO$: Calcd C 76.37; H 12.82; N 3.71 Found: C 76.32; H 12.91; N 3.67.

A 0.4M stock solution was prepared dissolving the title compound (3.02 g) in dichloromethane (12.9 ml) and kept for weeks in the refrigerator at 0° C. without any appreciable decomposition.

Starting from a solution of (+)-(2R,5S)-2-isopropyl-5-methyl-1-methylene cyclohexane obtained from (+)-menthone, following the same procedure as described above, di{[(1R,2R,5S)-2-isopropyl-5-methylcyclohex-1-yl] -methyl}boron bromide (Compound of formula VII: L=from (+)menthone; X=Br) was obtained.

EXAMPLE 20

N-tertbutoxycarbonyl-10-deacetyl-N-debenzoyl taxol (Taxotere)

(Compound of formula I: $R_2$=Ph; $R_2$=t-BuOCO; $R_3$=H)

A solution of 7,10-di(2,2,2-trichloroethyloxycarbonyl)-10-deacetyl-13-O-[(4S,5R)-N-tertbutoxycarbonyl-2,2-dimethyl-4-phenyl-1,3-oxazolidin-5-carbonyl]-baccatin (Compound IV: ---=single bond; $R_1$=Ph; $R_4$=$R_5$=Me; $R_7$=t-BuOCO; $R_8$=$R_9$=$CCl_3CH_2$—OCO—) (46 mg, 0.04 mmol) in methanol (1 ml) was treated with methanesulfonic acid (0.048 mmol) at room temperature. The reaction was monitored by TLC, and after several hours diluted with water, extracted with dichloromethane (×2), washed with water, dried over $Na_2SO_4$, and concentrated to give crude 7,10-di (2,2,2-trichloroethyloxycarbonyl)-10-deacetyl N-tertbutoxycarbonyl,N-debenzoyl taxol. This compound was dissolved in methanol (1 ml), and treated with acetic acid (1 ml) and powdered zinc (40 mg) at 60° C. for 1 hour to yield the title compound (25.96 mg, 76%).

EXAMPLE 21

Taxol (Compound of formula I: $R_1$=Ph; $R_2$=PhCO; $R_3$=Ac)

A solution of 7-(2,2,2-trichloroethyloxycarbonyl)-13-O-[ (4S,5R)-N-tertbutoxycarbonyl-2,2-dimethyl-4-phenyl-1,3-oxazolidin-5-carbonyl]-baccatin (Compound IV:---=single bond; $R_1$=Ph; $R_4$=$R_5$=Me; $R_7$=t-BuOCO; $R_8$=Ac; $R_9$=$CCl_3CH_2$—OCO—) (46 mg, 0.043 mmol) in formic acid (1 ml) was stirred at room temperature. The reaction was monitored by TLC, and after 4 hours diluted with water, extracted with dichloromethane (×2), washed with water, dried over $Na_2SO_4$, and concentrated to give crude 7-(2,2, 2-trichloroethyloxycarbonyl)-N-debenzoyl taxol. This compound was dissolved in ethyl acetate (1 ml), and treated with benzoyl chloride and aqueous sodium hydrogen carbonate to give crude 7-(2,2,2-trichloroethyloxycarbonyl) taxol. This compound was dissolved in methanol (1 ml), and treated with acetic acid (1 ml) and powdered zinc (40 mg) at 60° C. for 1 hour to yield the title compound (23.9 mg, 70%).

EXAMPLE 22

N-tertbutoxycarbonyl-10-deacetyl-N-debenzoyl taxol (Taxotere)

(Compound of formula I: $R_1$=Ph; $R_2$=t-BuOCO; $R_3$=H)

A solution of 7,10-di(2,2,2-trichloroethyloxycarbonyl)-10-deacetyl-13-O-[(4S,5R)-N-tertbutoxycarbonyl-2,2-dimethyl-4-phenyl-1,3-oxazolidin-5-carbonyl]-baccatin (Compound IV: ---=single bond; $R_1$=Ph; $R_4$=$R_5$=Me; $R_7$=t-BuOCO; $R_8$=$R_9$=$CCl_3CH_2$—OCO—) (46 mg, 0.038 mmol) in formic acid (1 ml) was stirred at room temperature. The reaction was monitored by TLC, and after 4 hours diluted with water, extracted with dichloromethane (×2), washed with water, dried over $Na_2SO_4$, and concentrated to give crude 7,10-di(2,2,2-trichloroethyloxycarbonyl)-10-deacetyl, N-debenzoyl taxol. This compound was dissolved in THF (1 ml), and treated with ditertbutyldicarbonate ($BOC_2O$) and aqueous sodium hydrogen carbonate to give crude 7,10-di(2,2,2-trichloroethyloxycarbonyl)-10-deacetyl, N-tertbutoxycarbonyl, N-debenzoyl taxol. This compound was dissolved in methanol (1 ml), and treated with acetic acid (1 ml) and powdered zinc (40 mg) at 60° C. for 1 hour to yield the title compound (19.13 mg, 566).

EXAMPLE 23

7-(2,2,2-Trichloroethyloxycarbonyl)-13-O-[(4S,5R)-N-tertbutoxycarbonyl-2,2-dimethyl-4-phenyl-1,3-oxazolidin-5-carbonyl]-baccatin (Compound of formula IV: ---=single bond; $R_1$=Ph; $R_4,R_5$=Me; $R_7$=t-BuOCO—; $R_8$=$CH_3CO$; $R_9$=$CCl_3$—$CH_2$—OCO—)

A solution of 7-Troc-baccatin III (27.4 mg, 0.036 mmol) and t-butyl [(4S,5R)-N-tertbutoxycarbonyl-2,2-dimethyl-4-phenyl-1,3-oxazolidin-5-yl]thiocarboxylate (49.6 mg, 0.126 mmol) in THF (0.72 ml) at 0° C. under argon, with stirring was treated with a freshly prepared 0.6M solution of lithium or sodium hexamethyldisilazide in THF-hexanes 62:38 (0.270 ml, 0.162 Tmnol). After 24 h stirring at 0° C., the mixture was quenched with a saturated $NH_4Cl$ aqueous solution (2 ml). The aqueous phase was extracted with ethyl ether (3×3 ml), and the combined organic extracts were dried ($Na_2SO_4$) and evaporated. The crude product was purified by flash chromatography (hexanes-ethyl acetate 65:35) to give pure 7-(2,2,2-trichloroethyloxycarbonyl)-13-O-[(4S, 5R) -N-tertbutoxycarbonyl-2,2-dimethyl-4-phenyl-1,3-oxazolidin-5-carbonyl]-baccatin (22.8 mg, 60%).

$[\alpha]_D^{25}$=-54.7° (c 0.7 in methanol).

Reported in the literature (Tetrahedron Lett. 1992, 33, 5185):

$[\alpha]_D^{25}$=-55.2° (c 0.53 in methanol).

$^1$H-NMR ($CDCl_3$) δ=1.11 (9H, br.s, t-Bu), 1.18 (3H, s, Me), 1.27 (3H, s, Me), 1.77 (3H, s, Me), 1.82 (3H, s, Me), 1.83 (3H, s, Me), 1.93 (3H, s, Me), 2.0 (3H, s, OCOMe), 2.2 (3H, s, OCOMe), 2.05 (1H, m, C6-H), 2.19 (2H, m, C14-H), 2.60 (1H, m, C6-H), 3.91 (1H, d, J=6.95 Hz, C3-H), 4.11 (1H, d, J=8.0 Hz, C20-H), 4.29 (1H, d, J=8.0 Hz, C20-H), 4.49 (1H, d, J=5.7 Hz, C2'-H), 4.65–5.05 (2H, m, C—H [troc]), 4.93 (1H, m, C5-H), 5.1 (1H, m, C3'-H), 5.60 (1H, dd, J=6.8, 10.8 Hz, C7-H), 5.65 (1H, d, J=6.95 Hz, C2-H), 6.26 (1H, m, C13-H), 6.36 (1H, s, C10-H), 7.20–7.40 (5H, m, Ar—H), 7.50–7.60 (3H, m, Ar—H), 8.02 (2H, d, J=8.0 Hz, Ar—H).

EXAMPLE 24

7,10-Di(2,2,2-trichloroethyloxycarbonyl)-10-deacetyl-13-O-[(4S,5R)-N-tertbutoxycarbonyl-2,2-dimethyl-4-phenyl-1,3-oxazolidin-5-carbonyl]-baccatin (Compound of formula IV: ---=single bond; $R_1$=Ph; $R_4,R_5$=Me; $R_7$=t-BuOCO—; $R_8,R_9$=$CCl_3$—$CH_2$—OCO—)

A solution of 7,10-di(2,2,2-trichloroethyloxycarbonyl)-10-deacetylbaccatin III [7,10-diTroc-10-DAB III] (24.4 mg, 0.027 mmol) and t-butyl [(4S,5R)-N-tertbutoxycarbonyl-2,2-dimethyl-4-phenyl-1,3-oxazolidin-5-yl]thiocarboxylate (40.0 mg, 0.101 mmol) in THF (0.545 ml) at 0° C. under argon, with stirring was treated with a freshly prepared 0.6M solution of lithium or sodium hexamethyldisilazide in THF-hexanes 62:38 (0.202 ml, 0.121 mmol). After 24 h stirring at 0° C., the mixture was quenched with a saturated $NH_4Cl$ aqueous solution (2 ml). The aqueous phase was extracted with ethyl ether (3×3 ml), and the combined organic extracts were dried ($Na_2SO_4$) and evaporated. The crude product was purified by flash chromatography (hexanes-ethyl acetate 6:4) to give pure 7,10-di (2,2,2-trichloroethyloxycarbonyl)-10-deacetyl-13-O-[(4S,5R)-N-tertbutoxycarbonyl-2,2-dimethyl-4-phenyl-1,3-oxazolidin-5-carbonyl]-baccatin (20.0 mg, 61%).

$[\alpha]_D^{25}$=-37.1° (c 1.0 in methanol)

Reported in the literature (Tetrahedron Lett. 1992, 33, 5185):

$[\alpha]_D^{25}$=-37.2° (c 1.0 in methanol).

$^1$H-NMR ($CDCl_3$) δ=1.10 (9H, br.s, t-Bu) , 1.17 (3H, s, Me) , 1.27 (3H, s, Me), 1.60 (3H, s, Me), 1.75 (3H, s, Me), 1.80 (3H, s, Me), 1.95 (3H, s, Me), 2.10 (3H, s, OCOMe), 2.05 (1H, m, C6-H), 2.20 (2H, m, C14-H), 2.60 (1H, m, C6-H), 3.90 (1H, d, J=6.95 Hz, C3-H), 4.10 (1H, d, J=8.30 Hz, C20-H), 4.28 (1H, d, J=8.30 Hz, C20-H), 4.50 (1H, d, J=5.5 Hz, C2'-H), 4.60 (1H, d, J=11.0 Hz, C—H [troc]), 4.65–4.90 (2H, m, C—H [troc']), 4.90 (1H, d, J=11.0 Hz, C—H [troc]), 4.95 (1H, m, C5-H), 5.1 (1H, m, C3'-H), 5.60 (1H, dd, J=6.8, 10.0 Hz, C7-H), 5.65 (1H, d, J=6.95 Hz, C2-H), 6.25 (1H, s, C10-H), 6.25 (1H, m, C13-H), 7.20–7.40 (5H, m, Ar—H), 7.50–7.60 (3H, m, Ar—H), 8.02 (2H, d, J=8.0 Hz, Ar—H).

EXAMPLE 25 t-Butyl [(4S,5R)-N-tertbutoxycarbonyl-2,2-dimethyl-4-phenyl-1,3-oxazolidin-5-yl]thiocarboxylate (Compound of formula II: ---=single bond; $R_1$=Ph; $R_4,R_5$=Me; $R_6$='Bu; $R_7$=t-BUOCO)

A solution of t-butyl (2R,3S)-3-tertbutoxycarbonylamino-2-hydroxy-3-phenylthiopropionate (0.060 g, 0.17 mmol) in toluene (8.0 ml) was treated with pyridinium p-toluene sulfonate (2.14 mg) and freshly distilled 2-methoxypropene (0.384 ml). The mixture was stirred at RT for 5 min, and at 80° C. for 4 h. After dilution with ethyl acetate (8 ml), the organic phase was washed with aqueous $NaHCO_3$ sat. solution (3 ml), brine (2×3 ml), dried ($Na_2SO_4$), and evaporated to give a crude mixture. Purification via flash chromatography (hexanes-ethyl ether 95:5) gave pure t-butyl [(4S,5R)-N-tertbutoxycarbonyl-2,2-dimethyl-4-phenyl-1,3-oxazolidin-5-yl]thiocarboxylate (42.5 mg, 65.6%).

$^1$H-NMR ($CDCl_3$ 50° C.) δ=1.19 (9H, s, t-Bu), 1.51 (9H, s, t-Bu), 1.73 (3H, s, Me), 1.79 (3H, s, Me), 4.37 (1H, d, J=5.0, CHO), 5.0 (1H, d, J=5.0 Hz, CHN), 7.2–7.4 (5H, m, Ar—H).

$^{13}$C-NMR ($CDCl_3$) selected peaks δ=26.147, 26.601, 27.918, 29.600, 47.764, 63.934, 87.156, 126.137, 127.361, 128.393, 151.472, 199.685.

IR ($CHCl_3$) selected peaks: 1702.84 cm$^{-1}$ [$v_{CO}$, stretching, t-BuSCO], 1672.00 cm$^{-1}$ [$v_{CO}$, stretching, t-BuO(CO)N].

EXAMPLE 26 t-Butyl 3-tertbutoxycarbonylamino-2-hydroxy-3-phenylthiopropionate (Compound of formula IX: $R_1$=Ph; $R_6$='Bu; $R_7$=t-BuOCO)

To a stirred solution of t-butyl (t-butyldimethylsilyloxy) thioacetate (0.701 g, 2.67 mmol) in ethyl ether (12.0 ml) at 0° C., under argon atmosphere a solution of di{[(1R,2R,5S)-2-isopropyl-5-methylcyclohex-1-yl]-methyl} boron bromide in dichloromethane (0.4M; 12.0 ml, 4.8 mmol), and then $Et_3N$ (0.706 ml, 5.07 nmol) were added dropwise. Enolborinate was generated with concurrent formation and precipitation of $Et_3N$—HBr. After 5 h at RT, the mixture was cooled to −78° C. and N-(trimethylsilyl)benzaldimine (PhCH=N—SiMe3) (0.710 g, 4.0 mmol) was added dropwise. The resulting mixture was stirred at −78° C. for 0.5 h, then slowly warmed to −5° C. during 2 h, and stirred at −5° C. overnight. The mixture was then quenched with pH 7 phosphate buffer (12 ml), and extracted with dichloromethane (3×10 ml). The combined organic extracts were dried ($Na_2SO_4$) and evaporated. The crude product was dissolved in 0.25N HCl in MeOH-$H_2O$ (1:1 v:v, 24 ml) and stirred at room temperature for 3 h. The resulting solution was evaporated to dryness and pumped in vacuum (0.1 mmHg) in a dessicator overnight over phosphorus pentoxide. The solid residue (1.074 g, 2.66 mmol) was then dissolved in dichloromethane (4.44 ml) and treated at 0° C. with triethylamine (1.48 ml, 10.64 mmol) and, after further 10 minutes, with ditertbutyldicarbonate (1.32 g, 6.03 mmol). The mixture was stirred at RT for 4 h, then quenched with NH$_4$Cl and extracted with dichlorometane (3×20 ml). The organic phase was washed with saturated brine, dried (Na$_2$SO$_4$), and evaporated. The crude reaction product was flash chromatographed (hexanes-ethyl ether 8:2) to give t-butyl 3-tertbutoxycarbonylamino-2-t-butyldimethylsilyloxy-3-phenyl thiopropionate (0.818 mg, 65.7% yield).

The syn-anti ratio of the mixture was determined by $^1$H-NMR analysis, by integration of the relevant peaks of the syn and anti isomers (70:30).

t-butyl (2R,3S)-3-tertbutoxycarbonylamino-2-t-butyldimethylsilyloxy-3-phenylthiopropionate [syn, 70% of the mixture]:

$^1$H-NMR (CDCl$_3$) δ=−0.47 (3H, s, MeSi), −0.1 (3H, s, MeSi), 0.85 (9H, s, $^t$BuSi), 1.43 (9H, s, $^t$Bu), 1.54 (9H, s, $^t$Bu), 4.22 (1H, br. s, CHOSi), 5.14 (1H, d, J=9.0 Hz, CHN), 5.59 (1H, d, NH, J=9.0 Hz), 7.19–7.33 (5H, m, Ar—H). t-butyl (2R,3R)-3-tertbutoxycarbonylamino-2-t-butyldimethylsilyloxy-3-phenylthiopropionate [anti 30% of the mixture]:

$^1$H-NMR (CDCl$_3$) selected peaks δ=−0.03 (3H, s, MeSi), 0.06 (3H, s, MeSi), 0.94 (9H, s, $^t$BuSi), 4.35 (1H, d, CHOSi, J=4.6 Hz), 4.95 (1H, m, CHN).

A solution of t-butyl 3-tertbutoxycarbonylamino-2-t-butyldimethylsilyloxy-3-phenylthiopropionate (syn:anti 70:30) (0.460 g, 0.985 mmol) in pyridine (49.8 ml) and acetonitrile (24.9 ml), under argon atmosphere was treated with a solution of Py (30%)-HF (70%) (Aldrich reagent) (11.7 ml) at room temperature. The mixture was warmed at 50° C. and stirred for 5 h. The solution was diluited with H$_2$O and extracted with ethyl acetate (3×50 ml). The combined organic extracts were washed with NaHCO$_3$ (3×25 ml) until pH 7, dried (Na$_2$SO$_4$) and evaporated. The mixture (syn:anti 70:30) was flash chromatographed (hexanes:ethyl ether 65:35) to give the analytically pure syn (0.170 mg) and anti (0.073 mg) diastereoisomers (yield 70%).

t-butyl (2R,3S)-3-tertbutoxycarbonylamino-2-hydroxy-3-phenylthiopropionate [syn]:

[α]$_D^{25}$=−8.7° (c 1.0 in CHCl$_3$)

$^1$H-NMR (CDCl$_3$) δ=1.44 (9H, s, $^t$Bu), 1.56 (9H, S, $^t$Bu), 3.56 (1H, br.s, OH), 4.43 (1H, br.s, CHO), 5.21 (1H, d, CHN, J=8.33 Hz), 5.43 (1H, d, NH, J=8.33 Hz), 7.25–7.46 (SH, m, Ar—H).

$^{13}$C NMR (CDCl$_3$) selected peaks δ=28.20, 29.66, 57.18, 79.88, 126.704, 127.440, 128.390, 139.154, 155.23, 201.97. t-butyl (2R,3R)-3-tertbutoxycarbonylamino-2-hydroxy-3-phenylthiopropionate [anti]:

$^1$H-NMR (CDCl$_3$) δ=1.42 (9H, s, $^t$Bu), 1.44 (9H, s, $^t$Bu), 3.26 (1H, d, OH, J=7.55 Hz), 4.57 (1H, dd, CHO, J=3.2, 7.55 Hz), 5.15 (1H, dd, CHN, J=3.2, 8.0 Hz), 5.55 (1H, d, NH, J=8.0 Hz), 7.20–7.40 (5H, m, Ar—H).

$^{13}$C NMR (CDCl$_3$) selected peaks δ=28.23, 29.6, 48.7, 79.29, 79.89, 155.07, 200.48.

Determination of the absolute configuration and of the enantiomeric excess of t-butyl (2R,3S)-3-tertbutoxycarbonylamino-2-hydroxy-3-phenylthiopropionate Chromatographed t-butyl (2R,3S)-3-tertbutoxycarbonylamino-2-hydroxy-3-phenylthiopropionate was saponified [a) 30% H$_2$O$_2$ (4 eq.), LiOH aq. (8 eq.), THF, 0° C., 15 h; b) Na$_2$SO$_3$] to give the corresponding acid. A solution of the acid in methanol was treated with a CH$_2$N$_2$ solution in ethyl ether to give the corresponding methyl (2R,3S)-3-tertbutoxycarbonylamino-2-hydroxy-3-phenylpropionate.

[α]$_D^{25}$=−7.6° (c 1.15 in CHCl$_3$).

Reported in the literature:

[α]$_D^{25}$=−7.0° (c 1.2 in CHCl$_3$) (J. Org. Chem. 1990, 55, 1957);

$^1$H-NMR (CDCl$_3$) δ=1.42 (9H, s, $^t$Bu), 3.2 (1H, br.s, OH), 3.84 (3H, s, OMe), 4.47 (1H, CHO, m), 5.21 and 5.36 (2H, br.d, NH and CHN), 7.25–7.40 (5H, m, Ar—H).

The % enatiomeric excess of was determined by $^1$H-NMR analysis of the Mosher ester derivatives. Methyl (2R,3S)-3-tertbutoxycarbonylamino-2-O-[(S)-α-methoxy-α-trifluoromethyl) phenyl]acetyl-3-phenylpropionate and methyl (2S,3R)-3-tertbutoxycarbonylamino-2-O-[(S)-(α-methoxy-α-trifluoromethyl) phenyl]acetyl-3-phenylpropionate were prepared and analysed as described in J. Org. Chem. 1994, 59, 1238. The 2R,3S: 2S,3R ratio was found to be ≧98:2.

EXAMPLE 27 t-Butyl (t-butyldimethylsilyloxy)thioacetate (Compound of formula VI: R$_6$=t-Bu; R$_{10}$=TBDMS)

Methyl glycolate (0.776 ml, 0.905 g, 10.0 nmol) was added to a suspension of TBDMS-Cl (1.81 g, 12.0 mmol) and imidazole (1.7 g, 25.0 mmol) in dry dimethylformamide (DMF) (2.0 ml) at 0° C., under stirring. After 90 min stirring at RT, water (25 ml) was added, and the resulting mixture was extracted with ethyl ether (3×15 ml). The organic phases were combined, washed with water (3×15 ml), dried (Na$_2$SO$_4$) and evaporated to give methyl (t-butyldimethylsilyloxy)acetate (2.0 g, 100%).

$^1$H-NMR (CDCl$_3$) δ=0.12 (6H, s, Me), 0.93 (9H, s, $^t$Bu), 3.75 (3H, s, OMe) , 4.26 (2H, s, CH$_2$).

A solution of AlMe3 (2.0M in hexanes, 8.82 ml, 17.64 mmol) in methylene chloride (35.28 ml) was treated at 0° C. with t-butylmercaptan (tBuSH) (1.99 ml, 17.64 mmol). After 20 min at 0°, a solution of methyl (t-butyldimethylsilyloxy) acetate (TBDMSOCH$_2$COOMe) (1.8 g, 8.82 mmol) in methylene chloride (4.41 ml) was added at −20° C. The mixture was stirred at −20° C. for 2 hr, then diluted with ethyl ether and quenched with 1.0N aqueous hydrochloric acid (10 ml). The organic phase was washed with 5% aqueous NaOH, saturated brine, dried (Na$_2$SO$_4$) and evaporated to give a crude mixture which was purified by flash chromatography (hexanes-methylene chloride 80:20) to afford pure t-butyl (t-butyldimethylsilyloxy) thioacetate (1.81 g, 78%).

$^1$H-NMR (CDCl$_3$) δ=0.10 (6H, s, Me), 0.94 (9H, s, $^t$BuSi), 1.47 (9H, s, $^t$BuS) , 4.16 (2H, s, CH$_2$)

We claim:

1. A process for preparing a compound of formula (I):

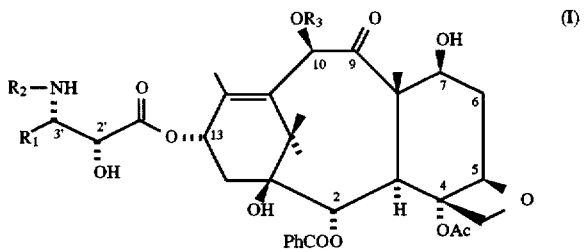

wherein:

$R_1$ is an aryl or heteroaryl group;

$R_2$ is hydrogen, arylcarbonyl, heteroarylcarbonyl or $C_1-C_6$ alkoxycarbonyl;

$R_3$ is hydrogen or acetyl;

the process comprising reacting a compound of formula (II):

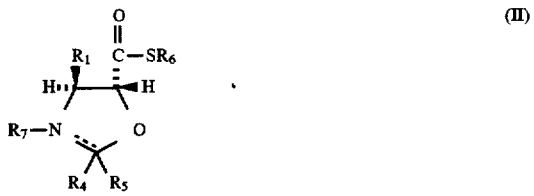

wherein:

R1 is defined above, the symbol --- represents a single or double bond, $R_7$ is $C_1-C_6$ alkoxycarbonyl, arylcarbonyl or heteroarylcarbonyl, each of $R_4$ and $R_5$ independently is hydrogen, $C_1-C_6$ alkyl, $C_1-C_6$ alkoxy, aryl or heteroaryl; and $R_6$ is $C_1-C_6$ alkyl, aryl or heteroaryl, provided that when the symbol --- is a double bond, $R_7$ and $R_4$ do not exist and $R_5$ is aryl or heteroaryl;

with a compound of formula (III):

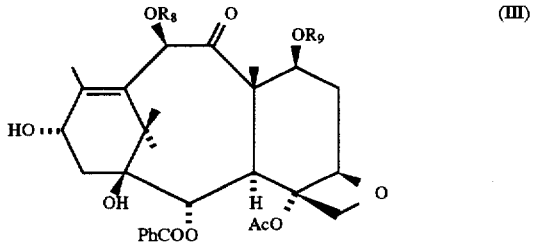

wherein each of $R_8$ and $R_9$ independently is a hydroxy protecting group, in the presence of a condensing agent, so obtaining a compound of formula (IV):

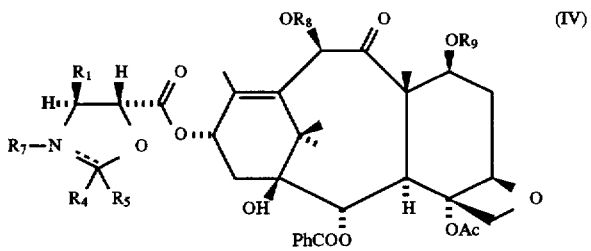

wherein:

$R_1$, $R_4$, $R_5$, $R_7$, $R_8$ and $R_9$, and the symbol --- are as defined above, provided that when --- is a double bond $R_7$ and $R_4$ do not exist and $R_5$ is aryl or heteroaryl; cleaving the five membered heterocyclic ring of the compound of formula IV and deprotecting the compound of formula (IV) under such conditions so as to produce the compound of formula (I), as defined above.

2. A process according to claim 1, for preparing a compound of formula (I) wherein $R_1$ is phenyl, 2-furyl, 4-pyridyl, 4-methoxyphenyl; $R_2$ is hydrogen, benzoyl, t-butoxycarbonyl, p-chlorophenylcarbonyl, p-methylphenylcarbonyl; $R_3$ is hydrogen, acetyl;

the process comprising reacting a compound of formula (II), as defined in claim 3, wherein the symbol --- is a single or a double bond, $R_1$ is as defined above;

each of $R_4$ and $R_5$ independently is hydrogen, $C_1-C_6$ alkyl, $C_1-C_3$ alkoxy, phenyl or a phenyl group substituted by one or more $C_1-C_4$ alkoxy group;

$R_6$ is a $C_1-C_4$ alkyl or phenyl or pyridyl;

$R_7$ is ethoxycarbonyl, n-propoxycarbonyl, n-butoxycarbonyl, t-butoxycarbonyl, benzoyl, p-chlorophenylcarbonyl, p-methylphenylcarbonyl, provided that when the symbol --- is a double bond, $R_7$ and $R_4$ do not exist and $R_5$ is phenyl or a phenyl group substituted by one or more $C_1-C_4$ alkoxy group, with a compound of formula (III), as defined in claim 1, wherein: $R_8$ is acetyl or 2,2,2-trichloroethoxycarbonyl;

$R_9$ is phenyldimethylsilyl, triethylsilyl, 2,2,2-trichloroethoxycarbonyl; in the presence of a condensing agent, to obtain a compound of formula (IV) as defined in claim 1 wherein the symbol --- and $R_1$, $R_4$, $R_5$, $R_7$, $R_8$ and $R_9$ are as defined above, cleaving the five membered heterocyclic ring of the compound of formula IV and deprotecting the compound of formula (1), as defined above.

3. A process according to claim 2, for preparing a compound of formula (I) as defined in claim I wherein: $R_1$ is phenyl; $R_2$ is benzoyl, t-butoxycarbonyl; $R_3$ is hydrogen or acetyl; said process comprising reacting a compound of formula (II), as defined in claim 1, wherein the symbol --- is a single or a double bond and $R_1$ is as defined above; each of $R_4$ and $R_5$ independently is hydrogen, methyl, ethyl, methoxy, phenyl, 2,4-dimethoxyphenyl, 3,4-dimethoxyphenyl or 4-methoxyphenyl; $R_6$ is t-butyl or phenyl; $R_7$ is benzoyl, or t-butoxycarbonyl; provided that when the symbol --- is a double bond, $R_4$ and $R_7$ do not exist and $R_5$ is phenyl, 2,4-dimethoxyphenyl, 3,4-dimethoxyphenyl or 4-methoxyphenyl; with a compound of formula (III) as defined in claim 1, wherein $R_8$ is acetyl or 2,2,2-trichloroethoxycarbonyl and $R_9$ is triethylsilyl or 2,2,2-trichloroethoxycarbonyl; in the presence of a condensing agent, to obtain a compound of formula (IV) wherein the symbol --- and $R_1$, $R_4$, $R_5$, $R_7$, $R_8$ and $R_9$ are as defined above, cleaving the five membered heterocyclic ring of the compound of formula IV and deprotecting the compound of formula (I), as defined above.

4. A process according to claim 1, wherein the condensing agent is NaH, n-BuLi, lithiumdiisopropylamide (LDA), $MNH_2$ or a compound of formula (V)

$$MN[Si(R)_3]_2 \qquad (V)$$

wherein R is a $C_1-C_4$ alkyl and M is Li, Na or K.

5. A process according to claim 1, wherein the condensing agent is a thiophilic metal salt.

6. A process according to claim 5, wherein the thiophilic metal salt is selected from triflates, trifluoroacetates, acetates and mesilates of Cu, Ag or Hg.

7. A compound of formula (II):

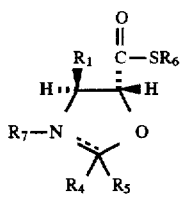

wherein:

the symbol --- represents a single or a double bond;

$R_1$ is aryl or heteroaryl;

each of $R_4$ and $R_5$ independently is hydrogen, $C_1$–$C_6$ alkyl, $C_1$–$C_3$ alkoxy, aryl or heteroaryl;

$R_6$ is $C_1$–$C_6$ alkyl, aryl or heteroaryl;

$R_7$ is $C_1$–$C_6$ alkoxycarbonyl, arylcarbonyl or heteroarylcarbonyl;

provided that when --- is a double bond $R_7$ and $R_4$ do not exist and $R_5$ is aryl or heteroaryl.

8. A compound of formula (II), according to claim 7, wherein:

the symbol --- is a single or a double bond;

$R_1$ is phenyl;

each of $R_4$ and $R_5$ independently is hydrogen, $C_1$–$C_6$ alkyl, $C_1$–$C_3$ alkoxy, phenyl or a phenyl group substituted with one ore more $C_1$–$C_4$ alkoxy group;

$R_6$ is $C_1$–$C_4$ alkyl, phenyl, or pyridyl;

$R_7$ is benzoyl, t-butoxycarbonyl;

provided that when --- is a double bond $R_4$ and $R_7$ do not exist and $R_5$ is phenyl or a phenyl group substituted with one or more $C_1$–$C_4$ alkoxy group.

9. A compound of formula (II), according to claim 8, wherein:

$R_1$ is phenyl;

each of $R_4$ and $R_5$ independently is hydrogen, methyl, ethyl, methoxy, phenyl, 2,4-dimethoxyphenyl, 3,4-dimethoxyphenyl or 4-methoxyphenyl;

$R_6$ is t-butyl or phenyl;

$R_7$ is t-butoxycarbonyl, benzoyl;

provided that when --- is a double bond $R_4$ and $R_7$ do not exist and $R_5$ is phenyl, 2,4-dimethoxyphenyl, 3,4-dimethoxyphenyl or 4-methoxyphenyl.

10. A process for preparing a compound of formula (II) according to claim 7, comprising:

a) reacting a compound of formula (VI):

$$R_{10}-O-CH_2-\overset{\overset{\displaystyle O}{\|}}{C}-SR_6 \quad (VI)$$

wherein $R_6$ is as defined in claim 7, and $R_{10}$ is arylcarbonyl, heteroarylcarbonyl, trialkylsilyl or 1-alkoxyalkyl, with a boron complex of formula (VII):

$$L_2BX \quad (VII)$$

wherein L is a chiral ligand and X is a halogen atom, and subsequently with a compound of formula (VIII):

$$R_1-CH=N-Z \quad (VIII)$$

wherein $R_1$ is as defined in claim 7, and Z is trialkylsilyl, $C_1$–$C_6$ alkoxycarbonyl, arylcarbonyl, heteroarylcarbonyl, optionally in the presence of an additional Lewis acid, and alternatively:

i) when $R_{10}$ is arylcarbonyl, or heteroarylcarbonyl, and $R_6$ is $C_1$–$C_6$ alkyl, transposing the arylcarbonyl or heteroarylcarbonyl from oxygen to nitrogen; or ii) reacting with $R_7Y$ wherein $R_7$ is as defined in claim 7 and Y is a leaving group after or before deprotecting the —$OR_{10}$ group to free hydroxy group;

so obtaining a compound of formula (IX)

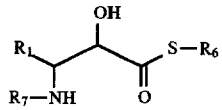

wherein $R_1$, $R_6$ and $R_7$ are as defined above; and b) cyclizing the compound of formula (IX) obtained above either:

b') by reacting the compound of formula (IX), prevailingly in the syn configuration, with a compound of formula (X), (XI) or (XII):

wherein $R_4$ and $R_5$ are as defined in claim 7 and $R_1I$ is a $C_1$–$C_3$ alkyl group, so obtaining a compound of formula (II) wherein the symbol --- is a single bond, and $R_1$, $R_4$, $R_5$, $R_6$, $R_7$ are as defined above;

or:

b") by reacting the compound of formula (IX), prevailingly in the anti configuration, with a dehydrating agent, so obtaining a compound of formula (II) wherein --- is a double bond, $R_7$ and $R_4$ do not exist and $R_5$ is aryl, heteroaryl.

11. A process according to claim 10 wherein Y is halide, azide or $OR_7$ wherein $R_7$ is as defined in claim 7.

12. A process as set forth in claim 1, said process further comprising preparing a first compound of formula (I) wherein $R_2$ is hydrogen and transforming said first compound of formula (I) into a second compound of formula (I) wherein $R_2$ is arylcarbonyl, heteroarylcarbonyl or $C_1$–$C_6$ alkoxycarbonyl, by acylating said first compound of formula (I) using an acylating agent selected from the group consisting of aroyl halide, heteroaroyl halide, and $C_1$–$C_6$ dialkyl dicarbonate.

13. A process as set forth in claim 2, said process further comprising preparing a first compound of formula (I) wherein $R_2$ is hydrogen and transforming said first compound of formula (1) into a second compound of formula (I) wherein $R_2$ is arylcarbonyl, heteroarylcarbonyl or $C_1$–$C_6$ alkoxycarbonyl, by acylating said first compound of formula (I) using an acylating agent selected from the group consisting of aroyl halide, heteroaroyl halide, and $C_1$–$C_6$ dialkyl dicarbonate.

14. A process as set forth in claim 3, said process further comprising preparing a first compound of formula (I) wherein $R_2$ is hydrogen and transforming said first compound of formula (1) into a second compound of formula (I) wherein $R_2$ is arylcarbonyl, heteroarylcarbonyl or $C_1$–$C_6$ alkoxycarbonyl, by acylating said first compound of formula (I) using an acylating agent selected from the group consisting of aroyl halide, heteroaroyl halide, and $C_1$–$C_6$ dialkyl dicarbonate.

* * * * *